(12) United States Patent
Iyappan et al.

(10) Patent No.: US 11,421,215 B2
(45) Date of Patent: Aug. 23, 2022

(54) NUCLEIC ACID ENCODING AN ISOMERASE, HOST CELLS CONTAINING THE NUCLEIC ACID, AND METHODS OF MAKING AND USING THE HOST CELLS

(71) Applicant: PETIVA PRIVATE LIMITED, Hyderabad (IN)

(72) Inventors: Saravanakumar Iyappan, Hyderabad (IN); Karthikeyan Venkata Narayanan, Hyderabad (IN); Banibrata Pandey, Hyderabad (IN)

(73) Assignee: PETIVA PRIVATE LIMITED, Punjagutta Hyderabad (IN)

( * ) Notice: Subject to any disclaimer, the term of this patent is extended or adjusted under 35 U.S.C. 154(b) by 0 days.

(21) Appl. No.: 17/044,583

(22) PCT Filed: Mar. 15, 2018

(86) PCT No.: PCT/IB2018/051738
§ 371 (c)(1),
(2) Date: Oct. 1, 2020

(87) PCT Pub. No.: WO2019/175636
PCT Pub. Date: Sep. 19, 2019

(65) Prior Publication Data
US 2021/0024914 A1 Jan. 28, 2021

(51) Int. Cl.
*C12N 9/92* (2006.01)
*C12P 19/24* (2006.01)
*C12P 41/00* (2006.01)

(52) U.S. Cl.
CPC .............. *C12N 9/92* (2013.01); *C12P 19/24* (2013.01); *C12P 41/00* (2013.01); *C12Y 503/01005* (2013.01)

(58) Field of Classification Search
None
See application file for complete search history.

(56) References Cited

U.S. PATENT DOCUMENTS

2011/0318801 A1* 12/2011 Kahsay .................. C12N 9/92
435/161

* cited by examiner

*Primary Examiner* — Christian L Fronda
(74) *Attorney, Agent, or Firm* — Sughrue Mion, PLLC

(57) ABSTRACT

The present invention provides for a nucleic acid encoding an isomerase and uses of the isomerase for bioconversion of sugar substrates. The invention represents an advancement in the field of enzyme engineering and discloses a modified nucleic acid for achieving optimum expression of a protein having isomerase activity in a heterologous host. The invention also discloses vectors carrying the modified nucleic acid and recombinant host cells carrying the vectors. The invention also discloses the process for producing a recombinant host cell, process for production of the recombinant enzyme and the process for bioconversion of sugars into their respective isomers using the recombinant protein.

15 Claims, 10 Drawing Sheets

Specification includes a Sequence Listing.

```
Modified  ATGAGTTATCAGCCGACGCCGAAGACCGCTTTACTTTTGGCCTGTGGACCGTTGGTTGG 60
Native    ATGAGCTACCAGCCCACCCCCGAGGACAGGTTCACGTTCGGACTCTGGACCGTCGGCTGG 60
          *****,**.*****,**.**.**.***.*.**.**.**.**.*********,**.***
Modified  CAGGGCCGTGACCGTTTGGTGACGCTACCCGTCGCGCACTGGATCCGGTGGAAACGGTT 120
Native    CAGGGAAGGGACCCGTTCGGCGACGCCACCCGCCGCGCCCTCGACCCGGTCGAGACGGTG 120
          *****,.*.*********,**.*****.*****.*****.**.**.*****.**.*****.
Modified  CAGCGTCTGGCAGAACTGGGTGCACATGGTGTTACCTTCCACGATGATGATCTGATTCCG 180
Native    CAGCGCCTGGCGGAACTCGGTGCCCACGGAGTGACCTTCCACGACGACGACCTGATCCCC 180
          *****.*****.*****.*****.**.**.**.**********.**.**.*****.**.
Modified  TTTGGCAGCTCTGATACGGAACGCGAATCTCATATCAAACGTTTTCGCCAGGCACTGGAT 240
Native    TTCGGTTCGTCGGACACCGAGCGCGAGTCGCACATCAAGCGGTTCCGCCAGGCCCTGGAC 240
          **.**...**.**.**.**.*****.**.**.*****.**.**.********.*****.
Modified  GCGACCGGCATGACGGTGCCGATGGCAACCACGAACCTGTTTACCCACCCGGTTTTCAAA 300
Native    GCCACCGGCATGACCGTCCCGATGGCCACCACGAACCTCTTCACGCACCCCGTCTTCAAG 300
          **.************.**.*******.********.**.**.*.*****.**.*****.
Modified  GATGGTGCCTTTACGGCAAATGATCGTGATGTGCGTCGCTATGCGCTGGGTAAAACCATT 360
Native    GACGGCGCGTTCACGGCCAACGACCGCGACGTGCGCCGCTACGCCCTCCGCAAGACGATC 360
          **.**.**.**.*****.**.**.**.**.*****.****.**.**.**.**.**.**.
Modified  CGCAACATCGATCTGGCGGCCGAACTGGGTGCAAAAACGTACGTGGCATGGGGTGGTCGT 420
Native    CGCAACATCGACCTGGCGGCCGAGCTGGGCGCGAAGACGTACGTCGCCTGGGGTGGCCGC 420
          ***********.***********.*****.**.**.*******.**.*******.**.
Modified  GAAGGTGCAGAAAGTGGTGCAGCGGAAAGATGTTCGTAGCGCGGCTGGATCGCATGAAGAA 480
Native    GAGGGCGCCGAGTCCGGCGCCGCCAAGGACGTGCGTTCCGCCCTGGACCGCATGAAGGAG 480
          **.**.**.**.**.**.**.**.**.**.**.***.**.**.**..**********.**.
Modified  GCCTTCGATCTGCTGGGCGAATATGTGACCAGTCAGGGTTACGATCTGCGTTTTGCGATT 540
Native    GCCTTCGACCTCCTCGGCGAGTACGTCACCTCGCAGGGCTACGACCTCCGCTTCGCCATC 540
          ********.**.**.*****.**.**.*****.*****.*****.**.*****.**.**.
Modified  GAACCGAAACCGAATGAACCGCGCGGCGATATCCTGCTGCCGACGGTTGTCATGCCCTG 600
Native    GAGCCCAAGCCGAACGAGCCCCGCGGCGACATCCTGCTGCCCACCGTCGGCACGCGCTG 600
          **.**.**.*****,**.**.*********.**********.**.**.**.**.***
Modified  GCATTCATTGAACGTCTGGAACGCCCCGGAACTGTATGGCGTGAACCCGGAAGTTGGTCAT 660
Native    GCCTTCATCGAGCGCCTGGAGCGGCCCGAGCTCTACGGCGTCAACCCCGAGGTCGGCCAC 660
          **.******.**.**.*****.**.***.**.**.*****.*****.**.**.**.**.
Modified  GAACAGATGGCCGGCCTGAATTTCCCGCACGGTATCGTACAGGCACTGTGGGCAGGCAAA 720
Native    GAGCAGATGGCCGGCCTGAACTTCCCCGCACGGCATCGCGCAGGCCTGTGGGCCGGGAAG 720
          **.*****************.*****,***,**,*****,*****,*********.**,
Modified  CTGTTCATATTGATCTGAACGGCCAGAGCGGTATCAAATATGATCAGGATCTGCGTTTC 780
Native    CTGTTCCACATCGACCTCAACGGCCAGTCCGGCATCAAGTACGACCAGGACCTGCGGTTC 780
          *****,**.**.**.**.*********.**.**.*****.**.*****.*****.***
Modified  GGCGCCGGTGATCTGCGCTCTGCATTTTGGCTGGTTGATCTGCTGGAAAGTGCCGGCTAC 840
Native    GGCGCGGGCGACCTGCGGTCCGCCTTCTGGCTGGTCGACCTCCTGGAGAGCGCCGGTTAC 840
          *****,**.**.*****.**.**.**.*******.**.**.**.**.**.*****,***
Modified  GAAGGTCCGCGTCACTTTGATTTCAAACCGCCGCGCACCGAAGATCTGGATGGCGTTTGG 900
Native    GAAGGACCGCGCCACTTCGACTTCAAGCCGCCGCGGACCGAGGACCTGACGGCGTGTGG 900
          *****,*****.*****,**,*****,********,*****,**,**,**,*****,***
```

FIGURE 2

```
Modified  GCGAGCGCCGCAGGTTGCATGCGTAATTACCTGATTCTGAAAGAACGTGCGGCCGCATTT 960
Native    GCCTCGGCGGCGGGCTGCATGCGCAACTACCTCATCCTGAAGGAGCGCGCGGCAGCCTTC 960
          **...,**.**.**.*******.**.*****.**.*****.**.**.*****.**.**.

Modified  CGTGCAGATCCGGAAGTGCAGGCAGCACTGCGTGCATCTCGTCTGGATCAGCTGGCACAG 1020
Native    CGCGCCGACCCCGAGGTGCAGGCGGCGCTGCGCGCCCTCGCGCCTGGACCAGCTGGCCCAG 1020
          **.**.**.**.**.********.**.*****.**.**.**.*****.********.***

Modified  CCGACCGCAGCAGATGGTCTGGAAGATCTGCTGGCGGATCGTGCCGCATTTGAAGATTTC 1080
Native    CCGACCGCGGCCGACGGCCTGGAGGACCTGCTCGCCGACCGCGCGGCCTTCGAGGACTTC 1080
          ********.**.**.**.*****.**.*****.**.**.**.**.**.**.**.***

Modified  GATGTTGAAGCGGCCGCAGCGCGCGGTATGGCATTTGAACGCCTGGACCAACTGGCTATG 1140
Native    GACGTGGAGGCCGCCGCCGCGCGCGGCATGGCCTTCGAACGCCTCGACCAGCTGGCGATG 1140
          **.**.**.**.**.*****.********.*****.**.********.*****.*****.***

Modified  GATCATCTGCTGGGTGCTCGTGGCTAA 1167
Native    GACCACCTGCTGGGCGCGCGGGGCTGA 1167
          **.**.********.**.**.****.*
```

FIGURE 2
Continued

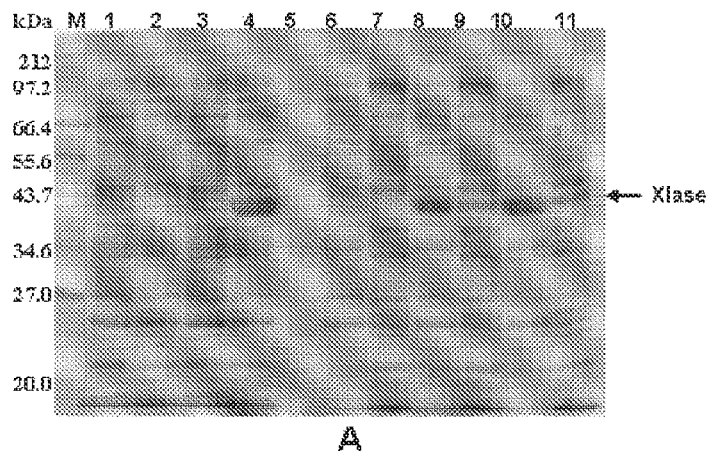

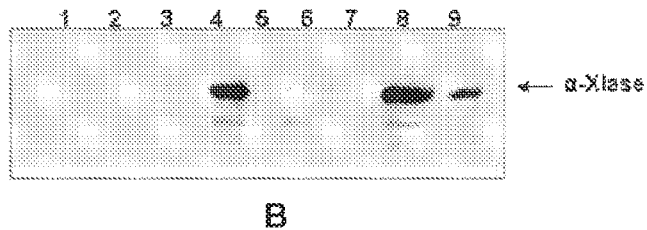

FIGURE 3

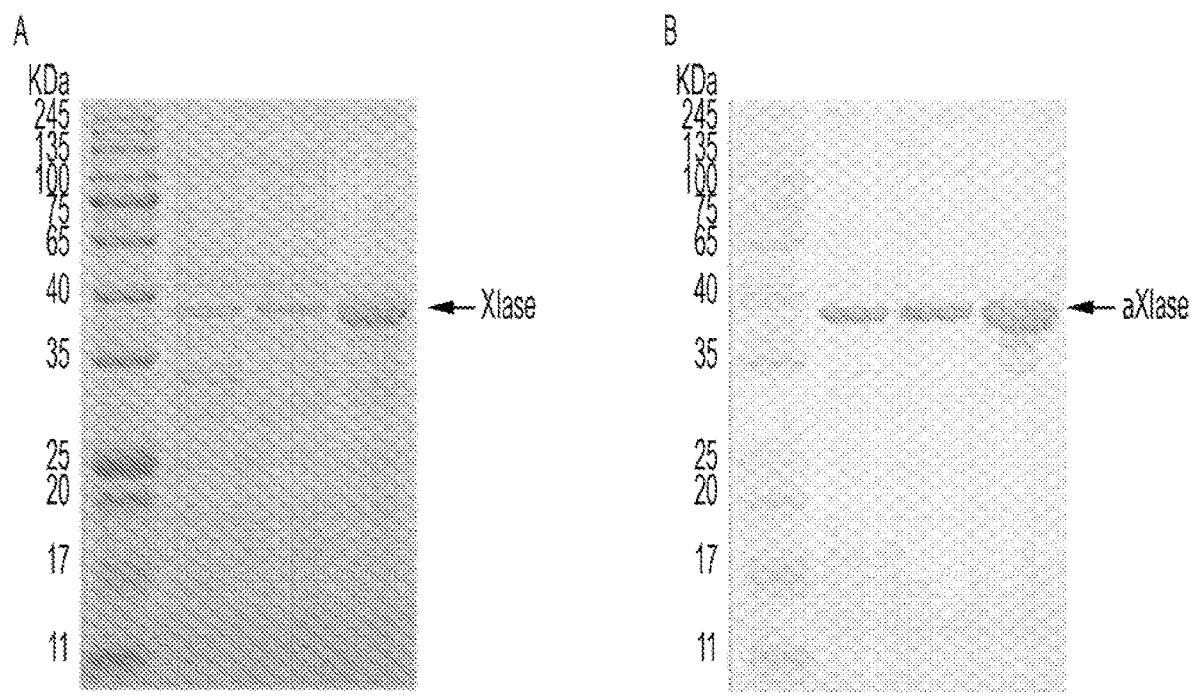
FIGURE 4
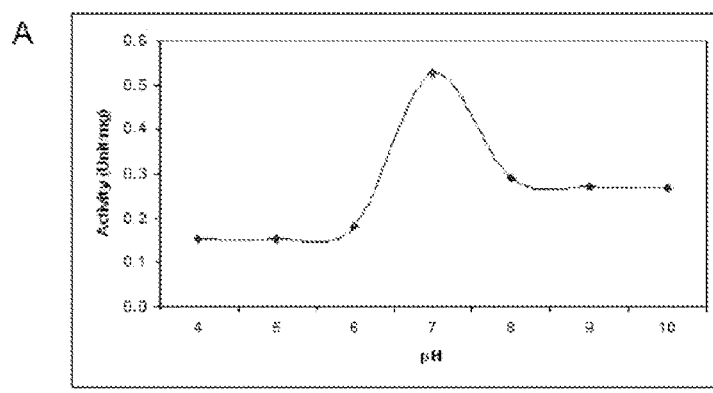
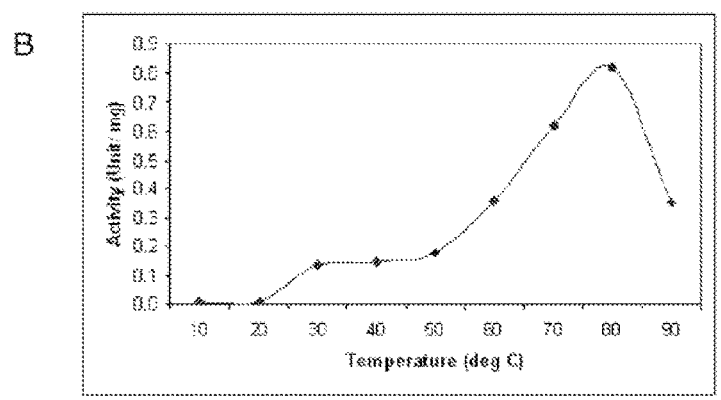
FIGURE 5

SEQUENCE LISTING

<160> NUMBER OF SEQ ID NOS: 5

<210> SEQ ID NO 1
<211> LENGTH: 1167
<212> TYPE: DNA
<213> ORGANISM: Artificial Sequence
<220> FEATURE:
<223> OTHER INFORMATION: Synthetic sequence, modified gene of Xylose
      Isomerase

<400> SEQUENCE: 1

| | | | | | |
|---|---|---|---|---|---|
| atgagttatc | agccgacgcc | ggaagaccgc | tttacctttg | gcctgtggac | cgttggttgg | 60 |
| cagggccgtg | acccgtttgg | tgacgctacc | cgtcgcgcac | tggatccggt | ggaaacggtt | 120 |
| cagcgtctgg | cagaactggg | tgcacatggt | gttaccttcc | acgatgatga | tctgattccg | 180 |
| tttggcagct | ctgatacgga | acgcgaatct | catatcaaac | gttttcgcca | ggcactggat | 240 |
| gcgaccggca | tgacggtgcc | gatggcaacc | acgaacctgt | tacccaccc | ggttttcaaa | 300 |
| gatggtgcct | ttacggcaaa | tgatcgtgat | gtgcgtcgct | atgcgctgcg | taaaaccatt | 360 |
| cgcaacatcg | atctggcggc | cgaactgggt | gcaaaaacgt | acgtggcatg | gggtggtcgt | 420 |
| gaaggtgcag | aaagtggtgc | agcgaaagat | gttcgtagcg | cgctggatcg | catgaaagaa | 480 |
| gccttcgatc | tgctgggcga | atatgtgacc | agtcagggtt | acgatctgcg | ttttgcgatt | 540 |
| gaaccgaaac | cgaatgaacc | gcgcggcgat | atcctgctgc | cgacggttgg | tcatgccctg | 600 |
| gcattcattg | aacgtctgga | acgcccggaa | ctgtatggcg | tgaacccgga | agttggtcat | 660 |
| gaacagatgg | ccggcctgaa | tttcccgcac | ggtatcgcac | aggcactgtg | ggcaggcaaa | 720 |
| ctgtttcata | ttgatctgaa | cggccagagc | ggtatcaaat | atgatcagga | tctgcgtttc | 780 |
| ggcgccggtg | atctgcgctc | tgcattttgg | ctggttgatc | tgctggaaag | tgccggctac | 840 |
| gaaggtccgc | gtcactttga | tttcaaaccg | ccgcgcaccg | aagatctgga | tggcgttttgg | 900 |
| gcgagcgccg | caggttgcat | gcgtaattac | ctgattctga | agaacgtgc | ggccgcattt | 960 |
| cgtgcagatc | cggaagtgca | ggcagcactg | cgtgcatctc | gtctggatca | gctggcacag | 1020 |
| ccgaccgcag | cagatggtct | ggaagatctg | ctggcggatc | gtgccgcatt | tgaagatttc | 1080 |
| gatgttgaag | cggccgcagc | gcgcggtatg | gcatttgaac | gcctggacca | actggctatg | 1140 |
| gatcatctgc | tgggtgctcg | tggctaa | | | | 1167 |

<210> SEQ ID NO 2
<211> LENGTH: 1167
<212> TYPE: DNA
<213> ORGANISM: Streptomyces corchorusii

<400> SEQUENCE: 2

| | | | | | |
|---|---|---|---|---|---|
| atgagctacc | agcccacccc | cgaggacagg | ttcacgttcg | gactctggac | cgtcggctgg | 60 |
| cagggaaggg | acccgttcgg | cgacgccacc | cgccgcgccc | tcgacccggt | cgagacggtg | 120 |
| cagcgcctgg | cggaactcgg | tgcccacgga | gtgaccttcc | acgacgacga | cctgatcccc | 180 |
| ttcggttcgt | cggacaccga | gcgcgagtcg | cacatcaagc | ggttccgcca | ggccctggac | 240 |
| gccaccggca | tgaccgtccc | gatggccacc | acgaacctct | tcacgcaccc | cgtcttcaag | 300 |
| gacgcgcgt | tcacggccaa | cgaccgcgac | gtgcgccgct | acgccctccg | caagacgatc | 360 |
| cgcaacatcg | acctggcggc | cgagctgggc | gcgaagacgt | acgtcgcctg | gggtggccgc | 420 |
| gagggcgccg | agtccggcgc | cgccaaggac | gtgcgttccg | ccctggaccg | catgaaggag | 480 |
| gccttcgacc | tcctcggcga | gtacgtcacc | tcgcagggct | acgacctccg | cttcgccatc | 540 |

```
gagcccaagc cgaacgagcc ccgcggcgac atcctgctgc ccaccgtcgg gcacgcgctg    600
gccttcatcg agcgcctgga gcggcccgag ctctacggcg tcaacccga ggtcggccac     660 gagcagatgg ccggcctgaa cttcccgcac ggcatcgcgc aggccctgtg ggccgggaag    720
ctgttccaca tcgacctcaa cggccagtcc ggcatcaagt acgaccagga cctgcggttc    780
ggcgcgggcg acctgcggtc cgccttctgg ctggtcgacc tcctggagag cgccggttac    840
gaaggaccgc gccacttcga cttcaagccg ccgcggaccg aggacctcga cggcgtgtgg    900
gcctcggcgg cgggctgcat cgcaactac ctcatcctga aggagcgcgc ggcagccttc     960
cgcgccgacc ccgaggtgca ggcggcgctg cgcgcctcgc gcctggacca gctggcccag   1020
ccgaccgcgg ccgacggcct ggaggacctg ctcgccgacc gcgcggcctt cgaggacttc   1080
gacgtggagg ccgccgccgc gcgcggcatg gccttcgaac gcctcgacca gctggcgatg   1140
gaccacctgc tgggcgcgcg gggctga                                       1167

<210> SEQ ID NO 3
<211> LENGTH: 6811
<212> TYPE: DNA
<213> ORGANISM: Artificial Sequence
<220> FEATURE:
<223> OTHER INFORMATION: Synthetic sequence, modified xylose isomerase
      encoding gene cloned in pET 11

<400> SEQUENCE: 3
ttctcatgtt tgacagctta tcatcgataa gctttaatgc ggtagtttat cacagttaaa     60
ttgctaacgc agtcaggcac cgtgtatgaa atctaacaat gcgctcatcg tcatcctcgg    120
caccgtcacc ctggatgctg taggcatagg cttggttatg ccggtactgc cgggcctctt    180
gcgggatatc cggatatagt tcctcctttc agcaaaaaac ccctcaagac ccgtttagag    240
gccccaaggg gttatgctag ttattgctca gcggtggcag cagccaactc agcttccttt    300
cgggctttgt tagcagccgg atccttagcc acgagcaccc agcagatgat ccatagccag    360
ttggtccagg cgttcaaatg ccataccgcg cgctgcggcc gcttcaacat cgaaatcttc    420
aaatgcggca cgatccgcca gcagatcttc cagaccatct gctgcggtcg gctgtgccag    480
ctgatccaga cgagatgcac gcagtgctgc ctgcacttcc ggatctgcac gaaatgcggc    540
cgcacgttct ttcagaatca ggtaattacg catgcaacct gcggcgctcg cccaaacgcc    600
atccagatct tcggtgcgcg gcggtttgaa atcaaagtga cgcggacctt cgtagccggc    660
actttccagc agatcaacca gccaaaatgc agagcgcaga tcaccggcgc cgaaacgcag    720
atcctgatca tatttgatac cgctctggcc gttcagatca atatgaaaca gtttgcctgc    780
ccacagtgcc tgtgcgatac cgtgcgggaa attcaggccg ccatctgtt catgaccaac     840 ttccgggttc acgccataca gttccggcg ttccagacgt tcaatgaatg ccagggcatg      900
accaaccgtc ggcagcagga tatcgccgcg cggttcattc ggtttcggtt caatcgcaaa    960
acgcagatct aaccctgac tggtcacata ttcgcccagc agatcgaagg cttctttcat    1020
gcgatccagc gcgctacgaa catctttcgc tgcaccactt tctgcacctt cacgaccacc   1080
ccatgccacg tacgtttttg cacccagttc ggccgccaga tcgatgttgc gaatggtttt   1140
acgcagcgca tagcgacgca catcacgatc atttgccgta aaggcaccat ctttgaaaac   1200
cgggtgggta acaggttcg tggttgccat cggcaccgtc atgccggtcg catccagtgc    1260
ctggcgaaaa cgtttgatat gagattcgcg ttccgtatca gagctgccaa acggaatcag   1320
atcatcatcg tggaaggtaa caccatgtgc acccagttct gccagacgct gaaccgtttc   1380
```

-continued

```
caccggatcc agtgcgcgac gggtagcgtc accaaacggg tcacggccct gccaaccaac    1440
ggtccacagg ccaaaggtaa agcggtcttc cggcgtcggc tgataactca tcatatgtat    1500
atctccttct taaagttaaa caaaattatt tctagagggg aattgttatc cgctcacaat    1560
tcccctatag tgagtcgtat taatttcgcg ggatcgagat ctcgatcctc tacgccggac    1620
gcatcgtggc cggcatcacc ggcgccacag gtgcggttgc tggcgcctat atcgccgaca    1680
tcaccgatgg ggaagatcgg gctcgccact tcgggctcat gagcgcttgt ttcggcgtgg    1740
gtatggtggc aggccccgtg gccggggggac tgttgggcgc catctccttg catgcaccat    1800
tccttgcggc ggcggtgctc aacggcctca acctactact gggctgcttc ctaatgcagg    1860
agtcgcataa gggagagcgt cgagatcccg gacaccatcg aatggcgcaa aacctttcgc    1920
ggtatggcat gatagcgccc ggaagagagt caattcaggg tggtgaatgt gaaaccagta    1980
acgttatacg atgtcgcaga gtatgccggt gtctcttatc agaccgtttc ccgcgtggtg    2040
aaccaggcca gccacgtttc tgcgaaaacg cgggaaaaag tggaagcggc gatggcggag    2100
ctgaattaca ttcccaaccg cgtggcacaa caactggcgg gcaaacagtc gttgctgatt    2160
ggcgttgcca cctccagtct ggccctgcac gcgccgtcgc aaattgtcgc ggcgattaaa    2220
tctcgcgccg atcaactggg tgccagcgtg gtggtgtcga tggtagaacg aagcggcgtc    2280
gaagcctgta aagcggcggt gcacaatctt ctcgcgcaac gcgtcagtgg gctgatcatt    2340
aactatccgc tggatgacca ggatgccatt gctgtgaaag ctgcctgcac taatgttccg    2400
gcgttatttc ttgatgtctc tgaccagaca cccatcaaca gtattatttt ctcccatgaa    2460
gacggtacgc gactgggcgt ggagcatctg gtcgcattgg gtcaccagca atcgcgctg    2520
ttagcgggcc cattaagttc tgtctcggcg cgtctgcgtc tggctggctg cataaatat    2580
ctcactcgca atcaaattca gccgatagcg gaacgggaag gcgactggag tgccatgtcc    2640
ggttttcaac aaaccatgca aatgctgaat gagggcatcg ttcccactgc gatgctggtt    2700
gccaacgatc agatgcgct gggcgcaatg cgcgccatta ccgagtccgg gctgcgcgtt    2760
ggtgcggata tctcggtagt gggatacgac gataccgaag acagctcatg ttatatcccg    2820
ccgttaacca ccatcaaaca ggattttcgc ctgctgggc aaaccagcgt ggaccgcttg    2880
ctgcaactct ctcagggcca ggcggtgaag gcaatcagc tgttgcccgt ctcactggtg    2940
aaaagaaaaa ccaccctggc gcccaatacg caaaccgcct ctccccgcgc gttggccgat    3000
tcattaatgc agctggcacg acaggtttcc cgactggaaa gcgggcagtg agcgcaacgc    3060
aattaatgta agttagctca ctcattaggc accgggatct cgaccgatgc ccttgagagc    3120
cttcaaccca gtcagctcct tccggtgggc gcggggcatg actatcgtcg ccgcacttat    3180
gactgtcttc tttatcatgc aactcgtagg acaggtgccg gcagcgctct gggtcatttt    3240
cggcgaggac cgctttcgct ggagcgcgac gatgatcggc ctgtcgcttg cggtattcgg    3300
aatcttgcac gccctcgctc aagccttcgt cactggtccc gccaccaaac gtttcggcga    3360
gaagcaggcc attatcgccg gcatggcggc cgacgcgctg ggctacgtct tgctggcgtt    3420
cgcgacgcga ggctggatgg ccttccccat tatgattctt ctcgcttccg gcggcatcgg    3480
gatgcccgcg ttgcaggcca tgctgtccag gcaggtagat gacgaccatc agggacagct    3540
tcaaggatcg ctcgcggctc ttaccagcct aacttcgatc actggaccgc tgatcgtcac    3600
ggcgatttat gccgcctcgg cgagcacatg gaacgggttg gcatggattg taggcgccgc    3660
cctataccct gtctgcctcc ccgcgttgcg tcgcggtgca tggagccggg ccacctcgac    3720
ctgaatggaa gccggcggca cctcgctaac ggattcacca ctccaagaat tggagccaat    3780
```

```
caattcttgc ggagaactgt gaatgcgcaa accaaccctt ggcagaacat atccatcgcg   3840
tccgccatct ccagcagccg cacgcggcgc atctcgggca gcgttgggtc ctggccacgg   3900
gtgcgcatga tcgtgctcct gtcgttgagg acccggctag gctggcgggg ttgccttact   3960
ggttagcaga atgaatcacc gatacgcgag cgaacgtgaa gcgactgctg ctgcaaaacg   4020
tctgcgacct gagcaacaac atgaatggtc ttcggtttcc gtgtttcgta aagtctggaa   4080
acgcggaagt cagcgccctg caccattatg ttccggatct gcatcgcagg atgctgctgg   4140
ctaccctgtg gaacacctac atctgtatta cgaagcgct ggcattgacc ctgagtgatt   4200
tttctctggt cccgccgcat ccataccgcc agttgtttac cctcacaacg ttccagtaac   4260
cgggcatgtt catcatcagt aacccgtatc gtgagcatcc tctctcgttt catcggtatc   4320
attaccccca tgaacagaaa tcccccttac acggaggcat cagtgaccaa acaggaaaaa   4380 accgcctta acatggcccg ctttatcaga agccagacat taacgcttct ggagaaactc   4440
aacgagctgg acgcggatga acaggcagac atctgtgaat cgcttcacga ccacgctgat   4500
gagctttacc gcagctgcct cgcgcgtttc ggtgatgacg gtgaaaacct ctgacacatg   4560
cagctcccgg agacggtcac agcttgtctg taagcggatg ccgggagcag acaagcccgt   4620
cagggcgcgt cagcgggtgt tggcgggtgt cggggcgcag ccatgaccca gtcacgtagc   4680
gatagcggag tgtatactgg cttaactatg cggcatcaga gcagattgta ctgagagtgc   4740
accatatatg cggtgtgaaa taccgcacag atgcgtaagg agaaaatacc gcatcaggcg   4800
ctcttccgct tcctcgctca ctgactcgct gcgctcggtc gttcggctgc ggcgagcggt   4860
atcagctcac tcaaaggcgg taatacggtt atccacagaa tcaggggata acgcaggaaa   4920
gaacatgtga gcaaaaggcc agcaaaaggc caggaaccgt aaaaaggccg cgttgctggc   4980 gttttccat aggctccgcc cccctgacga gcatcacaaa aatcgacgct caagtcagag   5040
gtggcgaaac ccgacaggac tataaagata ccaggcgttt ccccctggaa gctccctcgt   5100
gcgctctcct gttccgaccc tgccgcttac cggatacctg tccgcctttc tcccttcggg   5160
aagcgtggcg ctttctcata gctcacgctg taggtatctc agttcggtgt aggtcgttcg   5220
ctccaagctg ggctgtgtgc acgaaccccc cgttcagccc gaccgctgcg ccttatccgg   5280
taactatcgt cttgagtcca acccggtaag acacgactta tcgccactgg cagcagccac   5340
tggtaacagg attagcagag cgaggtatgt aggcggtgct acagagttct tgaagtggtg   5400
gcctaactac ggctacacta aaggacagt atttggtatc tgcgctctgc tgaagccagt   5460
taccttcgga aaaagagttg gtagctcttg atccggcaaa caaaccaccg ctggtagcgg   5520
tggttttttt gtttgcaagc agcagattac gcgcagaaaa aaaggatctc aagaagatcc   5580
tttgatcttt tctacggggt ctgacgctca gtggaacgaa aactcacgtt aagggatttt   5640
ggtcatgaga ttatcaaaaa ggatcttcac ctagatcctt ttaaattaaa aatgaagttt   5700
taaatcaatc taaagtatat atgagtaaac ttggtctgac agttaccaat gcttaatcag   5760
tgaggcacct atctcagcga tctgtctatt tcgttcatcc atagttgcct gactccccgt   5820
cgtgtagata actacgatac gggagggctt accatctggc cccagtgctg caatgatacc   5880
gcgagaccca cgctcaccgg ctccagattt atcagcaata aaccagccag ccggaagggc   5940
cgagcgcaga agtggtcctg caactttatc cgcctccatc cagtctatta attgttgccg   6000
ggaagctaga gtaagtagtt cgccagttaa tagtttcgc aacgttgttg ccattgctgc   6060
aggcatcgtg gtgtcacgct cgtcgtttgg tatggcttca ttcagctccg gttcccaacg   6120
```

-continued

| | |
|---|---|
| atcaaggcga gttacatgat cccccatgtt gtgcaaaaaa gcggttagct ccttcggtcc | 6180 |
| tccgatcgtt gtcagaagta agttggccgc agtgttatca ctcatggtta tggcagcact | 6240 |
| gcataattct cttactgtca tgccatccgt aagatgcttt tctgtgactg gtgagtactc | 6300 |
| aaccaagtca ttctgagaat agtgtatgcg gcgaccgagt tgctcttgcc cggcgtcaac | 6360 |
| acgggataat accgcgccac atagcagaac tttaaaagtg ctcatcattg gaaaacgttc | 6420 |
| ttcggggcga aaactctcaa ggatcttacc gctgttgaga tccagttcga tgtaacccac | 6480 |
| tcgtgcaccc aactgatctt cagcatcttt tactttcacc agcgtttctg ggtgagcaaa | 6540 |
| aacaggaagg caaaatgccg caaaaaaggg aataagggcg acacggaaat gttgaatact | 6600 |
| catactcttc ctttttcaat attattgaag catttatcag ggttattgtc tcatgagcgg | 6660 |
| atacatattt gaatgtattt agaaaaataa acaaataggg gttccgcgca catttccccg | 6720 |
| aaaagtgcca cctgacgtct aagaaaccat tattatcatg acattaacct ataaaaatag | 6780 |
| gcgtatcacg aggccctttc gtcttcaaga a | 6811 |

<210> SEQ ID NO 4
<211> LENGTH: 4814
<212> TYPE: DNA
<213> ORGANISM: Artificial Sequence
<220> FEATURE:
<223> OTHER INFORMATION: Synthetic sequence, modified xylose isomerase encoding gene cloned in pET23

<400> SEQUENCE: 4

| | |
|---|---|
| atccggatat agttcctcct ttcagcaaaa aacccctcaa gacccgttta gaggccccaa | 60 |
| ggggttatgc tagttattgc tcagcggtgg cagcagccaa ctcagcttcc tttcgggctt | 120 |
| tgttagcagc cggatctcag tggtggtggt ggtggtgctc gagtgcggcc gcaagctttt | 180 |
| agccacgagc acccagcaga tgatcccatag ccagttggtc caggcgttca atgccatac | 240 |
| cgcgcgctgc ggccgcttca acatcgaaat cttcaaatgc ggcacgatcc gccagcagat | 300 |
| cttccagacc atctgctgcg gtcggctgtg ccagctgatc cagacgagat gcacgcagtg | 360 |
| ctgcctgcac ttccggatct gcacgaaatg cggccgcacg ttctttcaga atcaggtaat | 420 |
| tacgcatgca acctgcggcg ctcgcccaaa cgccatccag atcttcggtg cgcggcggtt | 480 |
| tgaaatcaaa gtgacgcgga ccttcgtagc cggcactttc cagcagatca accagccaaa | 540 |
| atgcagagcg cagatcaccg cgcgccgaaac gcagatcctg atcatatttg ataccgctct | 600 |
| ggccgttcag atcaatatga acagtttgc ctgcccacag tgcctgtgcg ataccgtgcg | 660 |
| ggaaattcag gccggccatc tgttcatgac caacttccgg gttcacgcca tacagttccg | 720 |
| ggcgttccag acgttcaatg aatgccaggg catgaccaac cgtcggcagc aggatatcgc | 780 |
| cgcgcggttc attcggtttc ggttcaatcg caaaacgcag atcgtaaccc tgactggtca | 840 |
| catattcgcc cagcagatcg aaggcttctt tcatgcgatc cagcgcgcta cgaacatctt | 900 |
| tcgctgcacc actttctgca cctttcacgac cacccatgc cacgtacgtt tttgcaccca | 960 |
| gttcggccgc cagatcgatg ttgcgaatgg ttttacgcag cgcatagcga cgcacatcac | 1020 |
| gatcatttgc cgtaaaggca ccatctttga aaaccgggtg ggtaaacagg ttcgtggttg | 1080 |
| ccatcggcac cgtcatgccg gtcgcatcca gtgcctggca aaaacgtttg atatgagatt | 1140 |
| cgcgttccgt atcagagctg ccaaacggaa tcagatcatc atcgtggaag gtaacaccat | 1200 |
| gtgcacccca ttctgccaga cgctgaaccg tttccaccgg atccagtgcg cgacgggtag | 1260 |
| cgtcaccaaa cgggtcacgg ccctgccaac caacggtcca caggccaaag gtaaagcggt | 1320 |

```
cttccggcgt cggctgataa ctcatggatc cgcgacccat tgctgtcca ccagtcatgc   1380 tagccatatg tatatctcct tcttaaagtt aaacaaaatt atttctagag ggaaaccgtt   1440
gtggtctccc tatagtgagt cgtattaatt tcgcgggatc gagatctcgg gcagcgttgg   1500
gtcctggcca cgggtgcgca tgatcgtgct cctgtcgttg aggacccggc taggctggcg   1560
gggttgcctt actggttagc agaatgaatc accgatacgc gagcgaacgt gaagcgactg   1620
ctgctgcaaa acgtctgcga cctgagcaac aacatgaatg gtcttcggtt tccgtgtttc   1680
gtaaagtctg gaaacgcgga agtcagcgcc ctgcaccatt atgttccgga tctgcatcgc   1740
aggatgctgc tggctaccct gtggaacacc tacatctgta ttaacgaagc gctggcattg   1800
accctgagtg attttttctct ggtcccgccg catccatacc gccagttgtt taccctcaca   1860
acgttccagt aaccgggcat gttcatcatc agtaacccgt atcgtgagca tcctctctcg   1920
tttcatcggt atcattaccc ccatgaacag aaatcccccct tacacggagg catcagtgac   1980
caaacaggaa aaaccgcccc ttaacatggc ccgctttatc agaagccaga cattaacgct   2040
tctggagaaa ctcaacgagc tggacgcgga tgaacaggca gacatctgtg aatcgcttca   2100
cgaccacgct gatgagcttt accgcagctg cctcgcgcgt ttcggtgatg acggtgaaaa   2160
cctctgacac atgcagctcc cggagacggt cacagcttgt ctgtaagcgg atgccgggag   2220
cagacaagcc cgtcagggcg cgtcagcggg tgttggcggg tgtcggggcg cagccatgac   2280
ccagtcacgt agcgatagcg gagtgtatac tggcttaact atgcggcatc agagcagatt   2340
gtactgagag tgcaccatat atgcggtgtg aaataccgca cagatgcgta aggagaaaat   2400
accgcatcag cgctcttcc gcttcctcgc tcactgactc gctgcgctcg gtcgttcggc   2460
tgcggcgagc ggtatcagct cactcaaagg cggtaatacg gttatccaca gaatcagggg   2520
ataacgcagg aaagaacatg tgagcaaaag gccagcaaaa ggccaggaac cgtaaaaagg   2580
ccgcgttgct ggcgtttttc cataggctcc gcccccctga cgagcatcac aaaaatcgac   2640
gctcaagtca gaggtggcga aacccgacag gactataaag ataccaggcg tttccccctg   2700
gaagctccct cgtgcgctct cctgttccga ccctgccgct taccggatac ctgtccgcct   2760
ttctcccttc gggaagcgtg gcgctttctc atagctcacg ctgtaggtat ctcagttcgg   2820
tgtaggtcgt tcgctccaag ctgggctgtg tgcacgaacc ccccgttcag cccgaccgct   2880
gcgccttatc cggtaactat cgtcttgagt ccaacccggt aagacacgac ttatcgccac   2940
tggcagcagc cactggtaac aggattagca gagcgaggta tgtaggcggt gctacagagt   3000
tcttgaagtg gtggcctaac tacggctaca ctagaaggac agtatttggt atctgcgctc   3060
tgctgaagcc agttaccttc ggaaaaagag ttggtagctc ttgatccggc aaacaaacca   3120
ccgctggtag cggtggtttt tttgtttgca agcagcagat tacgcgcaga aaaaaaggat   3180
ctcaagaaga tcctttgatc ttttctacgg ggtctgacgc tcagtggaac gaaaactcac   3240
gttaagggat tttggtcatg agattatcaa aaaggatctt cacctagatc cttttaaatt   3300
aaaaatgaag ttttaaatca atctaaagta tatatgagta aacttggtct gacagttacc   3360
aatgcttaat cagtgaggca cctatctcag cgatctgtct atttcgttca tccatagttg   3420
cctgactccc cgtcgtgtag ataactacga tacgggaggg cttaccatct ggccccagtg   3480
ctgcaatgat accgcgagac ccacgctcac cggctccaga tttatcagca ataaaccagc   3540
cagccggaag ggccgagcgc agaagtggtc ctgcaacttt atccgcctcc atccagtcta   3600
ttaattgttg ccgggaagct agagtaagta gttcgccagt taatagtttg cgcaacgttg   3660
ttgccattgc tgcaggcatc gtggtgtcac gctcgtcgtt tggtatggct tcattcagct   3720
```

```
ccggttccca acgatcaagg cgagttacat gatcccccat gttgtgcaaa aaagcggtta      3780
gctccttcgg tcctccgatc gttgtcagaa gtaagttggc cgcagtgtta tcactcatgg      3840
ttatggcagc actgcataat tctcttactg tcatgccatc cgtaagatgc ttttctgtga      3900
ctggtgagta ctcaaccaag tcattctgag aatagtgtat gcggcgaccg agttgctctt      3960
gcccggcgtc aatacgggat aataccgcgc cacatagcag aactttaaaa gtgctcatca      4020
ttggaaaacg ttcttcgggg cgaaaactct caaggatctt accgctgttg agatccagtt      4080
cgatgtaacc cactcgtgca cccaactgat cttcagcatc ttttactttc accagcgttt      4140
ctgggtgagc aaaaacagga aggcaaaatg ccgcaaaaaa gggaataagg gcgacacgga      4200
aatgttgaat actcatactc ttcctttttc aatattattg aagcatttat cagggttatt      4260
gtctcatgag cggatacata tttgaatgta tttagaaaaa taaacaaata ggggttccgc      4320
gcacatttcc ccgaaaagtg ccacctgaaa ttgtaaacgt taatattttg ttaaaattcg      4380
cgttaaattt tgttaaatc agctcatttt ttaaccaata ggccgaaatc ggcaaaatcc      4440
cttataaatc aaaagaatag accgagatag ggttgagtgt tgttccagtt tggaacaaga      4500
gtccactatt aaagaacgtg gactccaacg tcaaagggcg aaaaccgtc tatcagggcg      4560 atggcccact acgtgaacca tcaccctaat caagtttttt ggggtcgagg tgccgtaaag      4620
cactaaatcg gaaccctaaa gggagccccc gatttagagc ttgacgggga agccggcga      4680 acgtggcgag aaaggaaggg aagaaagcga aaggagcggg cgctagggcg ctggcaagtg      4740
tagcggtcac gctgcgcgta accaccacac ccgccgcgct taatgcgccg ctacagggcg      4800
cgtcccattc gcca                                                       4814
```

<210> SEQ ID NO 5
<211> LENGTH: 388
<212> TYPE: PRT
<213> ORGANISM: Streptomyces corchorusii

<400> SEQUENCE: 5

```
Met Ser Tyr Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Arg
            20                  25                  30

Ala Leu Asp Pro Val Glu Thr Val Gln Arg Leu Ala Glu Leu Gly Ala
        35                  40                  45

His Gly Val Thr Phe His Asp Asp Leu Ile Pro Phe Gly Ser Ser
    50                  55                  60

Asp Thr Glu Arg Glu Ser His Ile Lys Arg Phe Arg Gln Ala Leu Asp
65                  70                  75                  80

Ala Thr Gly Met Thr Val Pro Met Ala Thr Thr Asn Leu Phe Thr His
                85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Ala Glu
        115                 120                 125

Leu Gly Ala Lys Thr Tyr Val Ala Trp Gly Gly Arg Glu Gly Ala Glu
    130                 135                 140

Ser Gly Ala Ala Lys Asp Val Arg Ser Ala Leu Asp Arg Met Lys Glu
145                 150                 155                 160

Ala Phe Asp Leu Leu Gly Glu Tyr Val Thr Ser Gln Gly Tyr Asp Leu
                165                 170                 175
```

```
Arg Phe Ala Ile Glu Pro Lys Pro Asn Glu Pro Arg Gly Asp Ile Leu
            180             185             190

Leu Pro Thr Val Gly His Ala Leu Ala Phe Ile Glu Arg Leu Glu Arg
        195             200             205

Pro Glu Leu Tyr Gly Val Asn Pro Glu Val Gly His Glu Gln Met Ala
    210             215             220

Gly Leu Asn Phe Pro His Gly Ile Ala Gln Ala Leu Trp Ala Gly Lys
225             230             235             240

Leu Phe His Ile Asp Leu Asn Gly Gln Ser Gly Ile Lys Tyr Asp Gln
            245             250             255

Asp Leu Arg Phe Gly Ala Gly Asp Leu Arg Ser Ala Phe Trp Leu Val
            260             265             270

Asp Leu Leu Glu Ser Ala Gly Tyr Glu Gly Pro Arg His Phe Asp Phe
            275             280             285

Lys Pro Pro Arg Thr Glu Asp Leu Asp Gly Val Trp Ala Ser Ala Ala
        290             295             300

Gly Cys Met Arg Asn Tyr Leu Ile Leu Lys Glu Arg Ala Ala Ala Phe
305             310             315             320

Arg Ala Asp Pro Glu Val Gln Ala Ala Leu Arg Ala Ser Arg Leu Asp
            325             330             335

Gln Leu Ala Gln Pro Thr Ala Ala Asp Gly Leu Glu Asp Leu Leu Ala
            340             345             350

Asp Arg Ala Ala Phe Glu Asp Phe Asp Val Glu Ala Ala Ala Ala Arg
            355             360             365

Gly Met Ala Phe Glu Arg Leu Asp Gln Leu Ala Met Asp His Leu Leu
        370             375             380

Gly Ala Arg Gly
385
```

NUCLEIC ACID ENCODING AN ISOMERASE, HOST CELLS CONTAINING THE NUCLEIC ACID, AND METHODS OF MAKING AND USING THE HOST CELLS

CROSS REFERENCE TO RELATED APPLICATIONS

This application is a National Stage of International Application No. PCT/IB2018/051738, filed Mar. 15, 2018.

FIELD OF INVENTION

The present disclosure relates to the field of enzyme engineering. More particularly, the invention relates to a novel nucleotide sequence encoding a protein exhibiting isomerase activity, vectors, recombinant cells and methods for isomerizing sugars.

BACKGROUND OF THE DISCLOSURE

Xylose isomerase, also known as glucose isomerase (GI) or fructose isomerase (FI) is an enzyme in having high industrial application and is amongst the highest tonnage value enzymes. Xylose isomerase has multiple functionality depending on the substrates and catalyzes the inter-conversion of D-xylose to D-xylulose, D-ribose to D-ribulose and D-glucose to D-fructose. The demand for this enzyme is mostly for preparation of high fructose syrup (HFS) and it has a high demand in the food industry.

Several attempts have been made to express xylose isomerase in heterologous as well as native hosts. However, the major constraint is low expression level within the host system which leads to low activity.

Further, mass production of xylose isomerase at industrial scale is challenging due to additional limitations associated with enzyme stability, fermentation and purification.

Commercial scale bioconversion process using biocatalysts requires mass production of enzymes. Due to the aforesaid limitations, production of xylose isomerase is a costly affair which in-turn increase the production cost of high value sugars.

The various approaches employed so far for a higher expression of xylose isomerase have been unsuccessful. The inventors have envisaged a unique approach by designing a novel nucleic acid for achieving a high level of expression of xylose isomerase having better activity under a wide range of physiological conditions efficient utilization of substrates.

Thus, the present invention solves a long-standing problem of providing an efficient, cheap and industrially-scalable means for production of xylose isomerase, which in turn lowers the cost of production of many rare-sugars.

SUMMARY OF THE DISCLOSURE

Technical Problem

The technical problem to be solved in this invention is to achieve industrial scale production of an enzyme having wide range of isomerase activity.

Solution to the Problem

The problem has been solved by inventing a novel nucleic acid and designing improved process for production of the isomerase enzyme.

Advantages of the Invention

The invention provides an improved nucleic acid, vectors and recombinant cells. Further, the invention provides methods for efficient, cheap and industrially-scalable means for production of the isomerase enzyme and improved processes for isomerizing sugars.

OVERVIEW OF THE INVENTION

The present invention relates to a modified nucleic acid encoding an isomerase enzyme which can be optimally expressed in a heterologous host. The invention provides for a recombinant vector containing a modified nucleic acid encoding an isomerase enzyme which can be optimally expressed in a prokaryotic host.

The invention also provides for a recombinant host cell which can optimally express an isomerase enzyme. The invention also provides for the development of recombinant strain containing the vector for optimal production of the isomerase enzyme.

Further, the invention provides a process for bioconversion of sugars into their respective isomers under a wide range of physiological conditions.

BRIEF DESCRIPTION OF DRAWINGS

The features of the present disclosure will become fully apparent from the following description taken in conjunction with the accompanying figures. With the understanding that the figures depict only several embodiments in accordance with the disclosure and are not to be considered limiting of its scope, the disclosure will be described further through use of the accompanying figures:

FIG. 2 illustrates sequence alignment analysis of modified gene sequence (SEQ ID NO: 1) with native gene sequence (SEQ ID NO: 2) encoding for the isomerase enzyme.

FIG. 3A depicts SDS-PAGE of cell fractions obtained from the recombinant strains and control strains.

FIG. 3B depicts the results of Western Blot analysis for identification of the protein obtained from recombinant strain.

FIG. 4A depicts different fractions and purified protein were separated on SDS-PAGE.

FIG. 4B depicts results of Western blot analysis using anti protein antibody.

FIG. 5A illustrates pH optima of the isomerase enzyme obtained from the recombinant strain.

FIG. 5B illustrates temperature optima of the isomerase enzyme obtained from the recombinant strain.

DETAILED DESCRIPTION OF THE INVENTION

Figure 1A:
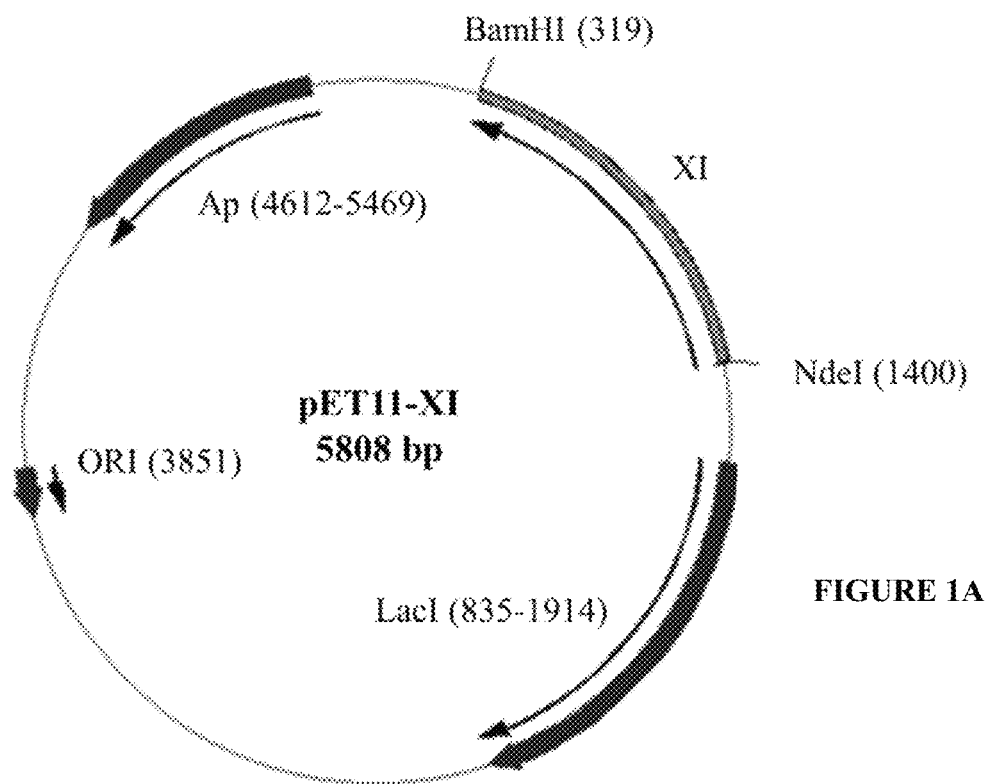
FIG. 1A illustrates the vector map of pET11-XI gene construct generated for expression of an isomerase enzyme in E. coli.

The present invention discloses a modified nucleic acid encoding an isomerase enzyme which is optimally expressed in a heterologous host.

The invention contemplates that the modified nucleic acid would have better expression in a heterologous host leading to better activity of the enzyme in the process of bioconversion.

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular as is considered appropriate to the context and/or application. The various singular/plural permutations may be expressly set forth herein for the sake of clarity.

Generally, nomenclatures used in connection with, and techniques of biotechnology, fermentation technology, genetic engineering and recombinant DNA technology described herein are those well-known and commonly used in the art. Certain references and other documents cited are expressly incorporated herein by reference. In case of conflict, the present specification, including definitions, will control. The materials, methods, figures and examples are illustrative only and not intended to be limiting.

Furthermore, the methods, preparation and use of the modified nucleic acid encoding the isomerase enzyme employ, unless otherwise indicated, conventional techniques in recombinant DNA technology, fermentation technology and related fields. These techniques, their principles, and requirements are explained in the literature and known to a person skilled in the art.

Before the method of generating the modified nucleic acid encoding the isomerase enzyme, vectors, recombinant hosts, application of said isomerase enzyme and other embodiments of the present disclosure are disclosed and described, it is to be understood that the terminologies used herein are for the purpose of describing particular embodiments only and are not intended to be limiting. It must be noted that, as used in the specification and the appended claims, the singular forms "a," "an" and "the" include plural referents unless the context clearly dictates otherwise.

As used herein, the term "comprises" or "comprising" is generally used in the sense to include, that is to say permitting the presence of one or more features or components.

As used herein, the term "disclosure" or "present disclosure" as used herein is a non-limiting term and is not intended to refer to any single embodiment of the particular disclosure but encompasses all possible embodiments as described in the specification and the claims.

As used herein, the term "xylose isomerase" or "XIase" refers to an enzyme that belong to intramolecular oxidoreductases group which catalyzes the inter-conversion of aldoses, ketoses and related compounds. These group of enzymes are classified as EC 5.3.1 as per classification done by Nomenclature Committee of the International Union of Biochemistry and Molecular Biology (NC-IUBMB). The enzyme disclosed in the present invention can catalyze the conversion of D-xylose into D-xylulose, D-glucose or D-mannose to D-fructose, D-galactose to D-tagatose, D-allulose to D-allose, D-rhamnose to D-rhamnulose and D-ribose to D-ribulose.

As used herein, the term "gene" refers to a nucleic acid fragment corresponding to specific amino acid sequence that expresses a specific protein with regulatory sequences. "Native gene" or "wild type gene" refers to a gene as found in nature with its own regulatory sequences.

As used herein, the term "promoter" refers to a region of DNA that initiates transcription of a particular gene. Promoters are located near the transcription start sites of genes, on the same strand and upstream on the DNA capable of controlling the expression of a coding sequence or functional RNA which can be native, derived or synthetic. Some promoters are called constitutive as they are active in all circumstances in the cell, while others are regulated becoming active in response to specific stimuli.

As used herein, the term "gene expression", refers to the process by which information from a gene is used in the synthesis of a functional gene product. These products are often proteins, but in non-protein coding genes such as transfer RNA (tRNA) or small nuclear RNA (snRNA) genes, the product is a functional RNA.

As used herein, the term "transformation" as used herein, refers to the transfer of a nucleic acid fragment into a host organism either in the form of plasmid or integrated stably to the chromosome of the host organisms resulting in genetically stable inheritance. A cloning vector is a small piece of DNA, mostly a plasmid, that can be stably maintained in an organism, and into which a foreign DNA fragment can be inserted for cloning or transformation purposes.

Although disclosure and exemplification has been provided by way of illustrations and examples for the purpose of clarity and understanding, it is apparent to a person skilled in the art that various changes and modifications can be practiced without departing from the spirit or scope of the disclosure. Accordingly, the foregoing descriptions and examples should not be construed as limiting the scope of the present disclosure.

As used herein, the term "immobilized enzyme reactor" refers to a reactor in which the reaction for producing sugar isomers is performed by an enzyme or microorganisms is adsorbed or linked to solid matrices Immobilization means that the substance providing a biological activity, in this case, isomerase or a microorganism including the same is immobilized on a solid immobilization carrier.

As used herein, the term "packed bed enzyme reactor" refers to a reactor in which the reaction for producing sugar isomers are performed by an enzyme immobilized on a carrier or through a strain immobilized on a carrier or through a column filled with an enzyme. The substance provides catalytic activity, in this case isomerase activity, particularly ketose or hexose isomerase activity.

As used herein, the term "membrane reactor" refers to a reactor in which the reaction for producing sugar isomers are performed by an enzyme trapped between the membranes having specified molecular cut of membrane whereas the substrate is passing through it. The enzyme in this case provides isomerase activity, particularly ketose or hexose isomerase activity.

The present invention discloses a modified nucleic acid encoding xylose isomerase (XIase) of *Streptomyces corchorusii* or *Streptomyces chibaensis* and having optimal expression levels in heterologous hosts.

In a preferred embodiment, the nucleic acid is represented by SEQ ID NO: 1.

In one aspect, the variant of xylose isomerase expressed encoded by the nucleic acid has not only xylose isomerase activity, but also, glucose isomerase activity, allulose isomerase activity and galactose isomerase activity.

The present disclosure also relates to a polypeptide encoded by the nucleic acid sequence as in SEQ ID NO: 1 or any variant thereof, wherein the polypeptide has sequence identity of at least about 70% identity with SEQ ID NO: 5.

In another aspect, the present disclosure discloses suitable vectors comprising the modified nucleic acid for optimal expression of the isomerase enzyme in a heterologous host. In yet another aspect, the vector of the disclosure is an expression vector which can be conveniently subjected to recombinant DNA procedures. The choice of vector will often depend on the host cell into which it is to be introduced. Thus, the vector could be an autonomously replicating vector, i.e. a vector which exists as an extra-chromosomal entity, the replication of which is independent of chromosomal replication, e.g. a plasmid. Alternatively, the vector could be one which, when introduced into a host cell, is integrated into the host cell genome, in part or in its entirety, and replicated together with the chromosomes into which it has been integrated.

In another aspect, the vector is preferably an expression vector in which the DNA sequence encoding the isomerase enzyme is operably linked to additional segments required for transcription of the DNA. The term, "operably linked" indicates that the segments are arranged so that they function in concert for their intended purposes, e.g. transcription initiates in some promoter and proceeds through the DNA sequence coding for the enzyme.

Preferably, the gene can be cloned into any *E. coli* expression vectors known in the art. In a preferred embodiment, the vector is a T7 vector.

Any suitable promoter can be used. In a preferred embodiment, an inducible promoter is used. The cloned gene sequences can be confirmed by restriction digestion or nucleotide sequencing.

In one embodiment, the nucleic acid has been cloned into a pET11a vector using NdeI and BamHI restriction enzyme sites to generate a recombinant plasmid. The nucleotide sequence of the recombinant plasmid is represented by SEQ ID NO: 3.

In another embodiment, the nucleic acid has been cloned into pET23a vector using BamHI and Hind III restriction enzymes to generate a recombinant plasmid expressing the isomerase enzyme with C-terminal 6× Histidine tag. The nucleotide sequence of the recombinant plasmid is represented by SEQ ID NO: 4.

In yet another embodiment, the vectors disclosed carry the modified gene in combination with highly inducible promoter, which is responsible for better expression of intracellular recombinant isomerase in a host not limiting to *E. coli*.

In another aspect, the gene sequence encoding the isomerase enzyme is modified for enhanced expression in a heterologous host, such as, but not limited to *Escherichia coli*.

In one aspect, the host-cell can be transformed with the vector of the present disclosure.

In an embodiment, the present disclosure provides a host cell comprising the vector having the modified nucleotide sequence for optimal expression of an isomerase enzyme in a heterologous host.

In another embodiment, the host cell into which the DNA construct or the recombinant vector of the disclosure is introduced may be any cell which can produce the present enzyme and includes yeast, bacteria, any other microorganism, a mammalian cell, plant cell or any cell culture of said category.

In a preferred embodiment, the host-cell is a bacterial cell selected from a group comprising *Escherichia coli, Bacillus subtilis, Lactococcus lactis, Bacillus megaterium, Pseudomonas putida* and *Corynebacterium glutamicum* or the host cell is a eukaryotic cell selected from a group comprising *Saccharomyces cerevisiae, Pichia pastoris* and *Hansenula polymorpha* or any host known in the art for expression of heterologous proteins using T7 promoter-based vectors for expression. In a preferred embodiment, the host-cell is *Escherichia coli* JM109.

Commercially available *E. coli* JM109 was used in the preferred embodiment of the invention. Stable recombinant strain containing the recombinant plasmid pET11-XI was selected and deposited in an international depository, namely MTCC, Chandigarh bearing accession numbers MTCC 5984 on 25 Apr. 2014.

In yet another embodiment, the recombinant enzyme is prepared by transfecting or transforming a host cell with a vector comprising a nucleotide sequence set forth as SEQ ID NO: 1. Variants of said sequence having at least 70% sequence identity fall under the ambit of the present disclosure.

In another embodiment, host cell when cultured in reactors/fermenters under suitable conditions provides for a recombinant isomerase as set forth as SEQ ID NO: 5 of the instant disclosure.

In a preferred embodiment, the disclosure provides optimum fermentation condition for mass production of enzymes in *E. coli*.

In another embodiment, the expression level of the gene was measured by quantifying the amount of recombinant enzyme. Standard techniques like Lowry protein assay, Bradford protein assay, BCA protein assay or Biuret protein assay may be performed for quantifying the protein present in the sample. The disclosure provides enhanced expression of the recombinant isomerase in *E. coli* in the range of 15% to 25%, precisely 20% (w/w) of the total cellular protein. In comparison with the expression level of the native xylose isomerase gene, it is found that the modification carried out in the native gene preferably resulted in 5-10% increase in the expression level.

Out of total expressed recombinant protein 70% to 90%, precisely 80% is found to be active soluble enzyme.

In another embodiment, for developing the antibody, the modified gene construct for expression of XIase is fused with 6×HIS epitope tag and expressed in *E. coli*. The expressed recombinant protein is purified by one step purification using an appropriate affinity matrix and method known to those skilled in the art. The pure protein is used as immunogen to generate polyclonal antibody in New Zealand white rabbits. The purified protein shows strong immunogenic response and anti-sera is collected and subjected to purification by affinity chromatography. Affinity purified XIase specific antibody is used in analytical methods mentioned in the embodiment.

In some embodiments, the synthesized protein is allowed to remain in the host cell and cultures of the recombinant host cell is employed.

In other embodiments, the protein is isolated or purified and then immobilized for subsequent applications.

In yet another embodiment, the disclosure relates to isolation and purification of more active enzymes from soluble proteins obtained from *E. coli* which is expressing the modified gene. The protein is purified using chromatography techniques such as, but not limited to, Q-Sepharose FF ion exchange column or any other technique using suitable matrices and method known to those skilled in the art.

In yet another embodiment, the protein of the present disclosure, when purified or expressed in a host cell has the capacity to catalyze the conversion of different pentose or hexose sugars to their respective isomer or epimer forms.

In still another embodiment, the present disclosure provides a process for producing corresponding isomer or epimer forms of sugars from their respective aldose or ketose sugars.

The present disclosure also provides a process for isomerizing a sugar substrate. The process comprises the steps of:
a) providing XIase according to the present disclosure; and
b) contacting the XIase with the sugar substrate under conditions such that the said substrate is converted into respective isomer or epimer of the sugar.

In a non-limiting embodiment, the sugar substrate is selected from a group comprising aldose or ketose sugars. In a preferable embodiment, the sugars are pentose or hexose sugars selected from a group comprising D-ribose, D-xylose, D-glucose, D-galactose, D-mannose, D-allulose and D-rhamnose.

In another embodiment, the concentration of sugar substrate employed is in the range of about 10% (w/v) to about 95% (w/v).

In yet another embodiment, the reactor is a packed bed reactor or an enzyme membrane reactor.

In yet another embodiment, the process conditions required for conversion of the sugar substrate involve maintaining temperature in the reactor between 30° C. and 80° C. and pH between 4 to 10.

In still another embodiment, the process provides for preparing a sugar composition and recovery of the same for nutraceutical applications.

In a preferred embodiment, the protein may be present as a whole cell biocatalyst or can be isolated with standard techniques such as cell disruption, filtration or any suitable method known to those skilled in the art. The protein may be used as an immobilized form using immobilization matrices and methods known to those skilled in the art.

In another embodiment of the present invention provides an immobilized enzyme reactor having isomerase activity for producing sugar isomers, comprising a column filled with a bed or solid matrices on which the purified or partially purified isomerase variant or the recombinant microorganism is immobilized.

As carriers for immobilizing the enzyme variant or the enzymes, any carriers capable of being used for immobilization of enzymes in the related art may be used without limitation. Preferably, ion-exchange based immobilization resins may be used. Amino modified resin known in the art such DuoliteA568™, ECR8415 or ECR8315 and ECR8415 (Lifetech™) can be used as well without limitation as immobilization support for this enzyme.

Yet another embodiment of the present invention provides a method for continuous production of sugar isomers by introducing a sugar solution into the packed bed enzyme reactor having immobilized isomerase enzyme or membrane reactor having isomerase enzyme.

In another embodiment, the protein of the present disclosure is used to catalyze the conversion of pentose or hexose sugars individually or in combination to their respective isomer or epimer forms.

In another embodiment, the recombinant isomerase enzyme is used in packed bed reactor or in an enzyme member reactor system for conversion/isomerization of the sugar substrates. Substrate solution ranging from 10% to 95% (w/v) concentration are fed at a predetermined flow rate for isomerization or epimerization of sugar such as pentose or hexose sugars individually or in combination to their respective isomer or epimer forms. The reactor temperature is maintained between 30° C. and 80° C. and the pH is maintained between 4 to 10. A subsequent step of extracting and purifying the products or the unutilized substrates after specific time period to recycle them in order to maximize the conversion of substrate to product, is performed. The separation of sugars is achieved using suitable chromatographic methods known in the art, such as, but not limited to simulated moving bed. The residual glucose may be removed by fermentation using yeast or with a suitable organism known to the person skilled in the related art for production of alcohols and separating the isomerized or epimerized sugars.

In still another embodiment, the present disclosure provides a process for producing D-fructose from D-glucose or D-mannose, D-xylulose from D-xylose, D-ribulose or D-arabinose from D-ribose, D-allose from D-allylose or D-psicose, D-tagatose from D-galactose and D-rhamnulose from D-rhamnose.

In a preferred embodiment, the present disclosure provides a process for producing D-xylulose from D-xylose, D-fructose from D-glucose, D-allose from D-allulose and D-tagatose from D-galactose using the enzyme obtained from modified gene in the present disclosure at varying pH and temperature.

In still another embodiment, the enzyme used in the process is stable up to about 145 hrs for continuous bioconversion.

In another embodiment, the invention relates to immobilization of the isomerase enzyme expressed by the modified nucleic acid using a suitable matrix. The immobilization of XIase is carried out by entrapment techniques using sodium alginate and bentonite. In this process 60% to 80%, more precisely 70% of the purified or partially purified isomerase enzyme is immobilized which is used in the bioconversion process.

Some advantages of the present invention are that the genetic modification of the native gene encoding for the isomerase enzyme proposed by the present disclosure results in an increase in expression levels of said enzyme in heterologous expression host cells in the range of 15%-25% of the total cellular protein. Additionally, 80%-90% of the recombinant isomerase enzyme produced by the host cells is soluble and active. Thus, the recombinant enzyme produced by the claimed process provides better yield than the methods disclosed in the prior art.

The enzyme produced in the instant disclosure is observed to convert different ketose and pentose sugars, specifically a rare sugar D-allulose (D-psicose) to D-allulose. D-allose is a cis-aldohexose which is a non-caloric sweetening and bulking agent which has good antioxidant properties. Till date, the production of D-allose was mainly achieved from D-psicose in a batch reaction by crude recombinant L-rhamnose isomerase. The present disclosure shows the novel function of the isomerase enzyme for industrial production of D-allose.

Another advantage of the present invention is that the enzyme disclosed can catalyze the conversion of D-galactose to D-tagatose, which was traditionally performed using the enzyme L-arabinose isomerase. Thus, the recombinant isomerase is multifunctional and can catalyze the isomerization of a large variety of substrates.

EXAMPLES

The following examples particularly describe the manner in which the invention is to be performed. But the embodiments disclosed herein do not limit the scope of the invention in any manner.

Example 1: Gene Construction

Gene encoding a multifunctional isomerase enzyme, namely, xylose isomerase was modified for enhanced expression in Escherichia coli JM109. The gene has been artificially synthesized using artificial gene synthesis approach known in the prior art. The modified gene sequence is represented as SEQ ID NO: 1. The polynucleotide sequence represented in SEQ ID NO: 1 was cloned into pUC57 using EcoRV restriction enzyme site to generate pUC57-XI. The cloned gene sequence was confirmed by restriction digestion and sequencing analysis.

The DNA fragment encoding the isomerase was PCR amplified using gene specific primers, and sub cloned into pET11a using NdeI and BamHI restriction enzyme sites to generate pET11-XI. Xylose Isomerase (XIase) gene is flanked by BglII, XbaI and NdeI at 5'-end, and BamHI at 3'-end. During cloning procedure NheI site is removed. The plasmid contains a T7 promoter, a T7 terminator and an ampicillin resistance marker. The vector map of the recombinant plasmid is represented in FIG. 1A.

Figure 1B:
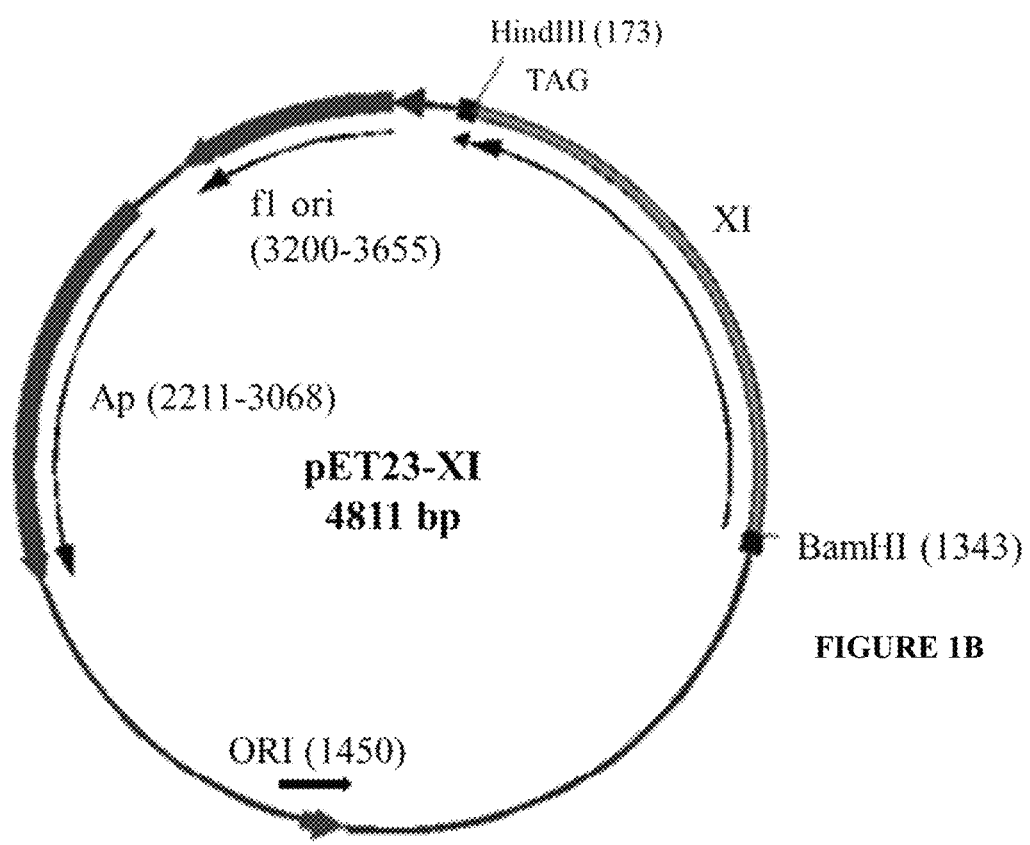
FIG. 1B illustrates the vector map of pET23-XI gene construct generated for expression of an isomerase enzyme in E. coli.

In addition, the xylose isomerase coding region was PCR amplified without stop codon using gene specific primers and sub cloned into E. coli expression vector pET23a using BamHI and Hind III restriction enzymes to generate pET23-XI-HIS construct expressing xylose isomerase with C-terminal 6× Histidine tag. The gene encoding the isomerase is flanked by BglII, XbaI, NdeI, NheI and BamHI at 5'-end, and HindIII, NotI and XhoI at 3'-end. During cloning procedure EcoRI, SacI and SalI sites are removed. The plasmid contains T7 promoter, T7 terminator, Epitope tag: 6× HIS and ampicillin resistance marker. The vector map of the recombinant plasmid is represented in FIG. 1B.

The recombinant plasmids carrying xylose isomerase encoding gene (pET11-XI and pET23-XI) were confirmed by restriction digestion analysis and followed by DNA sequencing.

Modified gene sequence (represented as "modified") was subjected to sequence alignment with native gene sequence (represented as "native") of Streptomyces chibaensis using multiple sequence alignment tool (ClustalW2). The nucleotides of modified gene sequence were marked as (.) and homology shared to native sequence was marked as (*). In the modified gene 23% of nucleotides were changed compared to native gene sequence. FIG. 2 illustrates sequence alignment analysis of modified gene sequence with native gene sequence encoding for XIase.

Example 2: Development of Recombinant Escherichia coli Strains with pET11 Vector for Production of Recombinant Enzyme Having Isomerase Activity Recombinant construct pET11-XI was transformed into E. coli expression host JM109 (DE3) by electro transformation method and grown on Luria-Bertani (LB) agar plates containing Ampicillin (50 µg/ml). Individual clones (JM109 [pET11-XI]) were picked and grown on LB media containing Ampicillin (75 µg/ml) for overnight at 37° C. Overnight culture was re-inoculated in LB (Amp+) media and grown up to 0.6 $OD_{600}$ and the cells were induced by addition of 0.5 mM IPTG (Isopropyl β-D-1-thiogalactopyranoside) and incubated at 37° C. An aliquot of E. coli culture was collected at different time points and the cell lysates were subjected to SDS-PAGE and Western blot analysis to verify the expression of recombinant isomerase.

The results of SDS-PAGE are depicted in FIG. 3A. For SDS-PAGE, the control and recombinant E. coli cells [JM109 carrying pET11-XI] are induced for protein expression by addition of 0.5 mM IPTG into media. Cells were lysed and the supernatant and pellet fractions were subjected to 12% SDS-PAGE using standard protocols. Control strain are depicted in Lane 1 and 2, which are uninduced and induced total cell lysate, respectively. Recombinant strains are depicted in Lane 3 and 4, which are uninduced and induced total cell lysate, respectively. Cell fractions of recombinant strains as depicted in Lane 6 and 7 are uninduced cell supernatant and pellet. Lane 8 and 9 contains 2 hr induced supernatant and pellet, respectively. Lane 10 and 11 contains 4 hr induced supernatant and pellet, respectively. Abbreviations used are M for Protein molecular weight marker and kDa for Kilo Dalton.

The results of the Western Blot are depicted in FIG. 3B. The protein from the recombinant strain was identified using Western Blot. The control strain, as depicted in Lane 1 and 2 are uninduced and induced total cell lysate, respectively. The recombinant strains, as depicted in Lane 3 and 4 are uninduced and induced total cell lysate, respectively. The cell fractions of recombinant strains as depicted in Lane 6 and 7 are uninduced cell supernatant and pellet, respectively. Lane 8 and 9 are 2 h induced supernatant and pellet, respectively Immuno-detection was carried our using protein specific antibodies.

Example 3: Development of Recombinant Escherichia coli Strains with pET23 Vector for Production of Recombinant Enzyme Having Isomerase Activity Recombinant construct pET23-XI was transformed into E. coli expression host BL21 (DE3) for production of the recombinant protein with C-terminal 6×HIS tag. Transformed clones (BL21 [pET23-XI]) were picked and grown on Luria-Bertani (LB) media containing Ampicillin (75 µg/ml) for overnight at 37° C. Overnight culture was re-inoculated in LB (Amp+) media and grown up to 0.6 $OD_{600}$ and the cells were induced by addition of 0.5 mM IPTG (Isopropyl β-D-1-thiogalactopyranoside) and incubated at 25° C. for 4-6 h. The cells were harvested, lysed, clarified and subjected to one step purification using Ni-NTA matrix for purification of the recombinant isomerase. The purified isomerase was used as immunogen to generate polyclonal antibody in New Zealand white rabbits.

The purified protein showed strong immunogenic response and antisera were collected and purified by affinity chromatography. The purified recombinant isomerase-specific antibody was used in analytical methods mentioned in the embodiment. This result shows that the protein having isomerase activity has been produced by the recombinant cells.

Example 4: Production of Recombinant Enzyme by Employing pET11 Vector Construct For optimum fermentation of recombinant *E. coli* (JM109 [pET11-XI]) and production of the recombinant protein, different media components and conditions were tested at shake flask level. Terrific broth (TB) media or defined media was used for production of the recombinant protein in fermenters. The components of terrific media broth are 24 g/L yeast extract, 12 g/L tryptone, 2.2 g/L potassium dihydrogen orthophosphate, 9.4 g/L dipotassium hydrogen orthophosphate and 0.4% glycerol. The components of the defined medium are 4 g/L $(NH_4)_2HPO_4$, 13.3 g/L $KH_2PO_4$, 1.7 g/L Citric acid, 10 g/L Yeast extract (pH 6.9) and trace elements (1.0 g/L $CaCl_2.6H_2O$, 6.0 g/L $MnCl_2.4H_2O$, 0.8 g/L $CuSO_4.5H_2O$, 1.2 g/L $H_3BO_3$, 0.8 g/L $NaMoO_4$, 13.52 g/L $Zn(CH_3COO)_2$, 40 g/L Fe-citrate), 14 g/L EDTA and 12 g/L $MgSO_4$. Glucose was used as carbon source and liquor ammonia was used as an alkali and nitrogen source. Ampicillin was used as antibiotic in inoculum development and during fermentation process. The fermenter was maintained at 37° C. with an agitation rate which was steadily increased from 250 to 1200 rpm, aeration rate being increased progressively from 0.6 to 2.4 scfm and maintaining dissolved oxygen (DO) at a concentration greater than 40%.

When the $OD_{600}$ of the culture reached 10-15, the feed was connected at 37.5 ml/hr (25 ml/L/hr) flow rate. When $OD_{600}$ of the culture reached 50-80, 1 mM isopropyl-beta-D-thiogalactopyranoside (IPTG) was added to the reactor to induce protein expression, and the fermentation was continued for another 8-10 hrs.

The said enzyme can directly be employed or isolated and purified as below and then employed for conversion or isomerization of sugar substrates into their respective isomer or epimer form.

Example 5: Isolation and Purification (Preparation) of the Recombinant Protein The recombinant protein having isomerase activity produced in *E. coli* was harvested from host cells after fermentation. The host cells resuspended in lysis buffer were lysed or disrupted by passing the cells twice through a high-pressure homogenizer at 18-20 KPsi. The cell lysate was clarified by centrifugation at 27000×g for 45 min at 4° C. The cell lysate supernatant containing the recombinant protein was purified or partially purified or directly used as an enzyme source for bioconversion of ketose and hexose sugars. FIGS. 4A-4B illustrate analysis of purified XIase. The recombinant XIase from soluble fraction was partially purified using Q-Sepharose column.

FIG. 4A depicts different fractions and purified protein were separated on 12% SDS-PAGE and stained by Coomassie brilliant blue R250.

Same fractions were separated on 12% SDS-PAGE and transferred onto nitrocellulose membrane and subjected to Western blot analysis using anti protein antibody as depicted in FIG. 4B. Lane 1 depicts supernatant fraction of induced cell, Lane 2 depicts clarified Supernatant fraction and Lane3 depicts Purified protein fractions. Abbreviations used are M for Protein molecular weight marker and kDa for Kilo Dalton.

The amount of recombinant protein was consequently quantified. Quantification was done by employing standard protocols. The results of protein quantification assays reveal that the recombinant protein in sample is present in the range of 15% to 25%, precisely 20% (w/w) of the total cellular protein.

The recombinant protein was studied to determine the pH and temperature optima for the same. The reaction mixture containing D-fructose and purified recombinant isomerase were incubated at different pH (FIG. 5A) and temperature (FIG. 5B). After bioconversion, the reaction was stopped by boiling the reaction mixture at 95° C. It was found that the enzyme had high activity between pH of 6-8, highest at 7.0. It was also found that recombinant isomerase had the highest activity between the temperature 60-90° C., highest at around 80° C. The results are depicted in FIGS. 5A-5B.

Example 6: Preparation and Operation of Packed Bed Reactor for Bioconversion Packed bed column is jacketed from the outside to supply hot water or steam or cold water to maintain the temperature. The arrangement for feeding the reactor is either from top or from the bottom and connected with valve to control the feed rate.

The recombinant isomerase immobilized beads are packed in a jacketed column. For preparation of immobilized beads, the recombinant protein having isomerase activity is mixed with equal volume of sodium alginate (about 3.7%) and bentonite (about 0.3%). The protein and carrier mixture are dropped into chilled 0.2 M $CaCl_2$ solution of volume 3 times to that of lysate and sodium alginate-bentonite mixture by any suitable means such as surgical needle with constant stirring. The immobilized beads are kept in $CaCl_2$ for overnight at about 4° C. The beads are collected and washed with distilled water and dried on a blotting paper at 4° C.

Alternatively, the recombinant protein is passed to jacketed column packed with immobilization matrices at room temperature at flow rate of 200±20 cm/h (40±1 min residence time). The substrate solution of concentration 10% to 70% (w/v) prepared in water contains 5 mM $MnCl_2$ or $MgCl_2$ and $CoCl_2$ (pH is adjusted to 8) or in 20 mM Tris-Hcl buffer containing 5 mM $MnCl_2$ and/or $MgCl_2$ and $CoCl_2$, pH 8.0 is pre-warmed (50° C.-60° C.) and is passed through the packed bed reactor from top to bottom direction with (8±2 min residence time). The product is collected and subjected to downstream processing.

Packed bed reactor is connected to downstream processing unit such as simulated moving bed and evaporator for separating and concentrating the sugars for recycling for maximizing the end product compositions.

Example 7: Preparation and Operation of Enzyme Membrane Reactor for Bioconversion Bioconversion is performed in a jacketed continuous stirred tank reactor equipped with a regenerated cellulose molecular weight cut-off membrane (10 kDa). The reactor is loaded with purified recombinant isomerase enzyme. The enzyme membrane reactor is operated at 60° C. with a magnetic stirrer rotating at 200 rpm and using 10%-70% (w/v) substrate solution prepared in water containing 5 mM MnCl2 (pH is adjusted to 8) or in 20 mM Tris-Hcl buffer containing 5 mM MnCl2, pH 8.0. The product is collected and subjected to downstream processing.

Example 8: Production of D-xylulose from D-xylose

Figure 10A:
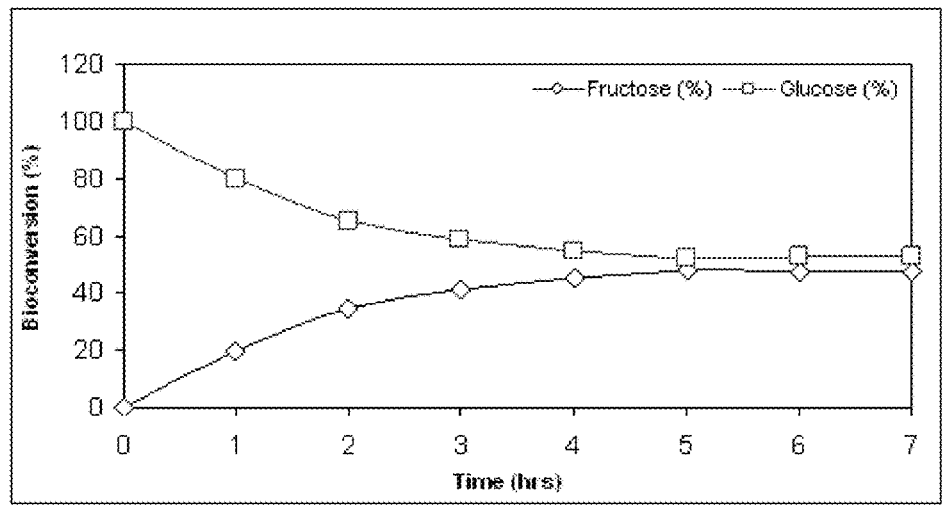
FIG. 10A illustrates bioconversion kinetics of conversion of D-glucose into D-fructose using the immobilized isomerase enzyme.
Figure 10B:
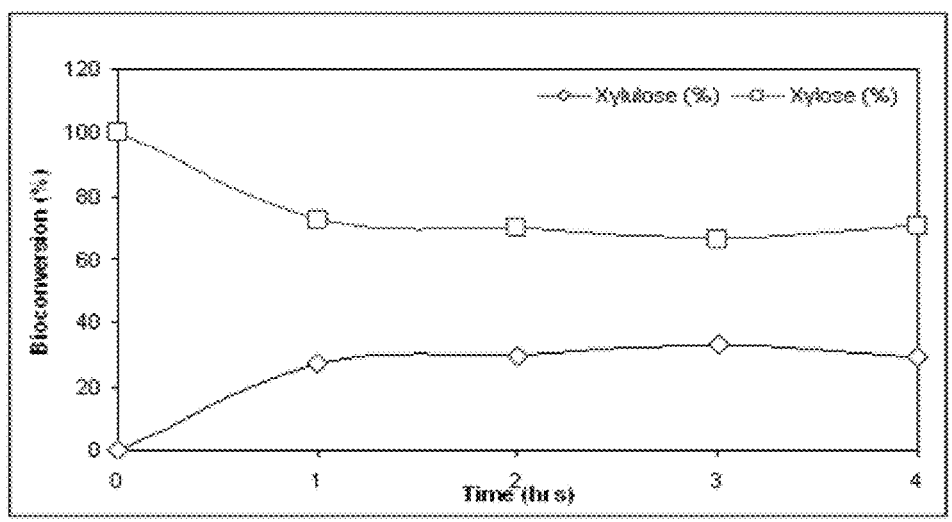
FIG. 10B illustrates bioconversion kinetics of conversion of D-xylose into D-xylulose using the immobilized isomerase enzyme.

The recombinant protein having isomerase activity prepared from *E. coli* was immobilized by using techniques known in the prior art or directly contacted with D-xylose solution for production of D-xylulose. In the present case, the enzyme was immobilized. The bioconversion conditions comprise maintaining the D-xylose substrate concentration between 20% and 95% (w/v) and using 100 to 1000 Units of the recombinant isomerase. For the present embodiment, the substrate was taken at a concentration of 100 g/L and 625 Units of the immobilized enzyme was used. Bioconversion reaction was carried out in 20 mM Tris-HCl buffer containing 5 mM $MnCl_2$ at a temperature of about 60° C. and at pH 8.0. The conversion of D-xylose to D-xylulose reached saturation at higher substrate concentration, preferably between 40% to 50% (w/v) at enzyme concentration of 600 to 650 units of enzyme with reaction time of about 6 h. The conversion rapidly reached around 22%, calculated as D-xylulose as a percentage of the reaction mixture. The reaction time for D-xylose to D-xylulose formation ratio is about 1 h to 3 h and the substrate to product formation ratio is about 73:27, 70:30 and 66:34 after 1 h, 2 h and 3 h respectively. The results of the bioconversion are depicted in FIG. 10B.

Figure 6A:
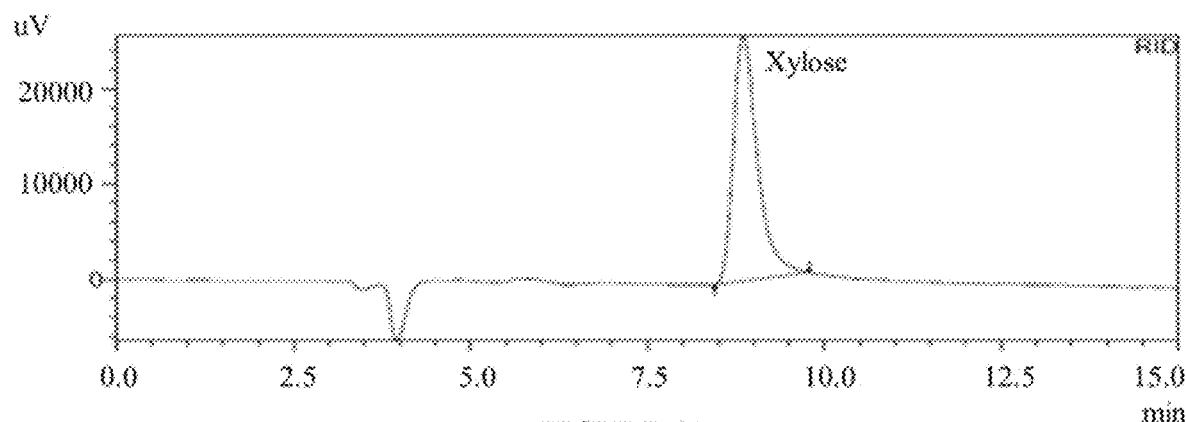
FIGS. 6A-6C illustrate HPLC analysis of D-xylose to D-xylulose conversion.
Figure 6B:
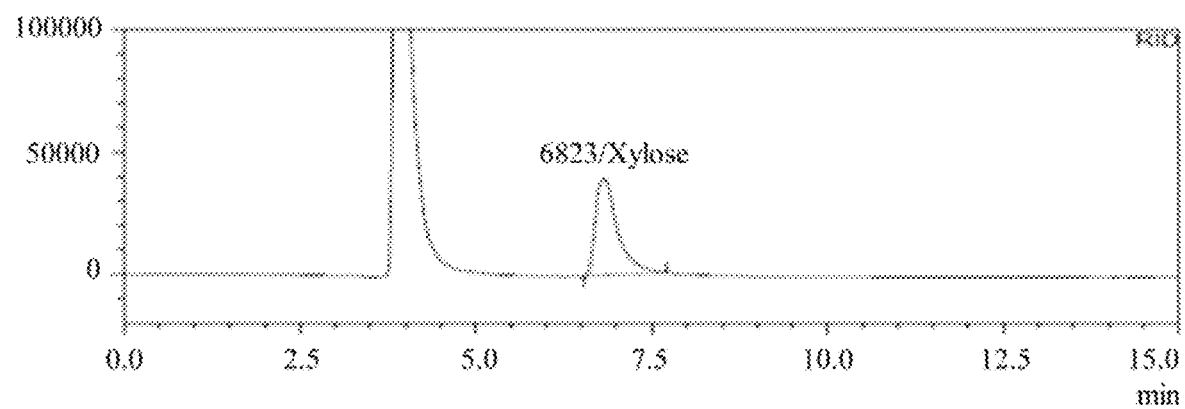
Figure 6C:
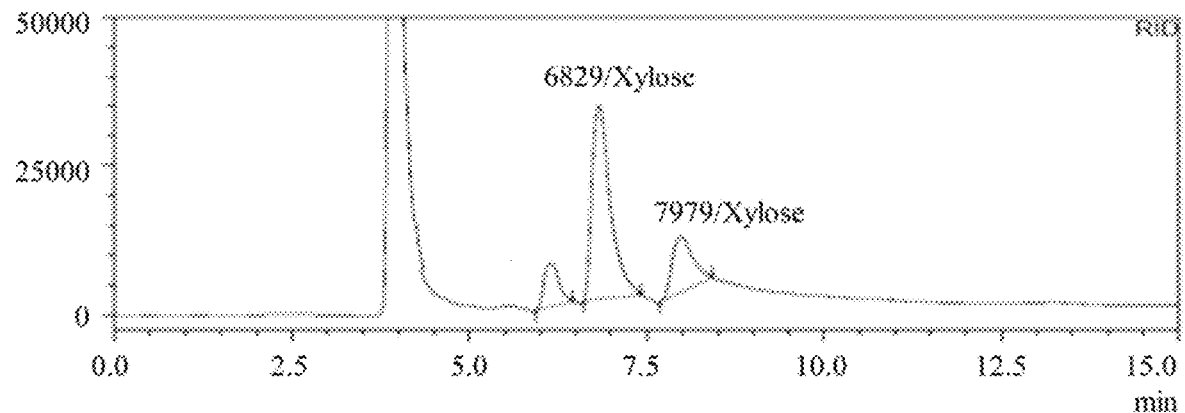

The reaction mixture was subjected to HPLC analysis to confirm the residual substrate and product formation. The product peaks were confirmed with commercially available D-xylose and D-xylulose (Sigma Aldrich) as substrate and product standards, respectively. The results of the studies are depicted in FIGS. 6A-6C. FIG. 6A exhibits the D-xylose standard chromatogram, FIG. 6B exhibits D-xylulose standard chromatogram and FIG. 6C depicts D-xylose and D-xylulose bioconversion mixture chromatogram.

Example 9: Production of D-fructose from D-glucose

The recombinant protein having isomerase activity prepared from *E. coli* was immobilized by using techniques known in the prior art or directly contacted with D-glucose solution for production of D-fructose. The bioconversion conditions comprise maintaining the D-glucose substrate at concentration between 20% and 95% (w/v) and using 100 to 1000 Units of the recombinant isomerase. For the present embodiment, the substrate was taken at a concentration of 100 g/L and 625 Units of immobilized enzyme was used. Bioconversion reaction was carried out in 20 mM Tris-HCl buffer containing 5 mM $MnCl_2$ at pH 8.0 and at a temperature of about 60° C. The conversion of D-glucose to D-fructose reached saturation at higher substrate concentration, preferably between 40% and 50% at enzyme concentration of 625 units of enzyme with reaction time of about 6 h. The reaction time for conversion of D-glucose to D-fructose is about 3 to 5 h and the substrate to product formation ratio is about 80:20, 65:35, 59:41, 55:45 and 52:48 after about 1 h, 2 h, 3 h, 4 h and 5 h respectively. The conversion rapidly reached around 42%, calculated as D-fructose as a percentage of reaction mixture within 3 h to 4 h of reaction. The results of the bioconversion are depicted in FIG. 10A.

Figure 7A:
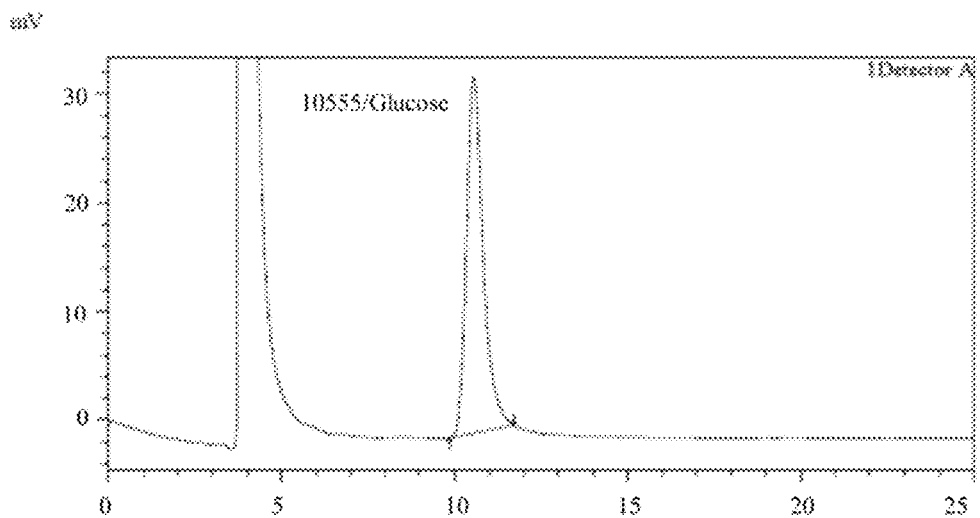
FIGS. 7A-7C illustrate HPLC analysis of D-glucose to D-fructose conversion.
Figure 7B:
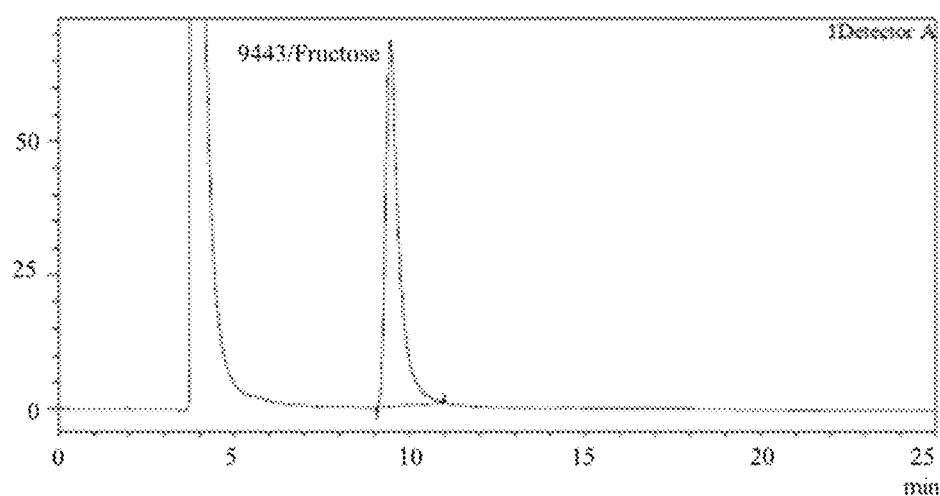
Figure 7C:
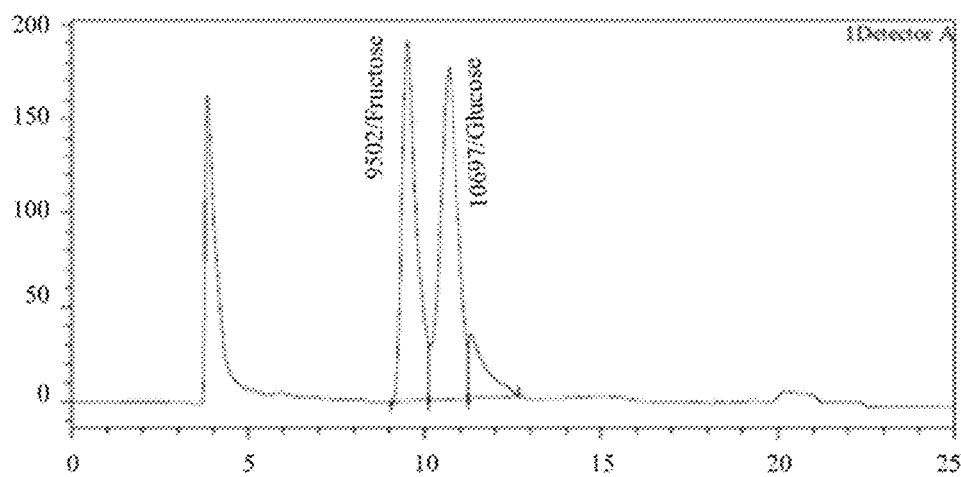

The reaction mixture was subjected to HPLC analysis to confirm the residual substrate and product formation. The product peaks were confirmed with commercially available D-glucose and D-fructose (Sigma Aldrich) as substrate and product standards, respectively. The results of the studies are depicted in FIGS. 7A-7C. FIG. 7A exhibits D-glucose standard chromatogram, FIG. 7B exhibits D-fructose standard chromatogram; and FIG. 7C exhibits D-glucose and D-fructose bioconversion mixture chromatogram.

Example 10: Production of D-allose from D-allulose

Figure 11:
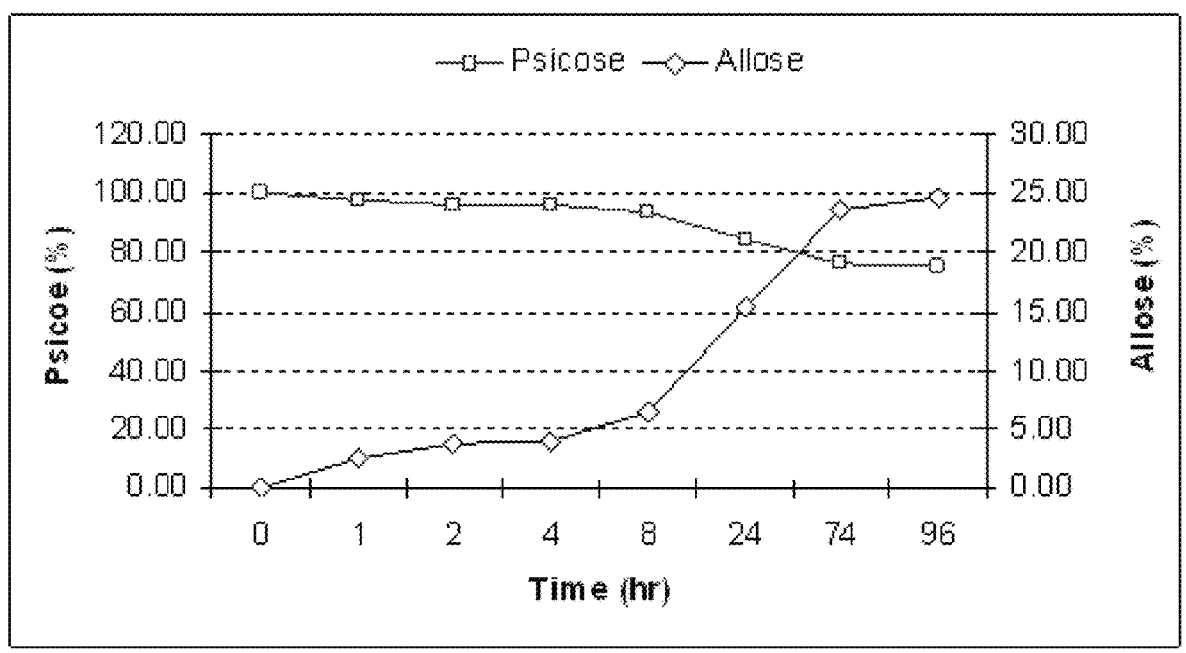
FIG. 11 illustrates bioconversion kinetics of conversion of D-psicose (D-allulose) into D-allose using the immobilized isomerase enzyme.

The recombinant protein having isomerase activity prepared from *E. coli* was immobilized by using techniques known in the prior art or directly contacted with D-allulose (D-psicose) solution for production of D-allose. The bioconversion conditions comprise maintaining the D-allulose substrate concentration between 20% and 95% (w/v) and 100 to 1000 units of the recombinant isomerase. For the present embodiment, the substrate was taken at a concentration of 100 g/L and 500 Units of the immobilized enzyme was used. Bioconversion reaction was carried out in 20 mM Tris-HCl buffer containing 5 mM $MnCl_2$ at pH 8.0 at temperature between 60° C. The conversion of D-allulose to D-allose reached saturation at higher substrate concentration, preferably between 40% to 50% (w/v) at enzyme concentration between 400 to 600, preferably 500 units of enzyme with reaction time of about 6 h. The reaction time for conversion of D-allulose to D-allose formation ratio is between 4-6 h and substrate to product formation ratio is about 95:05, 85:15 and 75:25 after about 1 h, 2 h and 4 h respectively. The conversion rapidly reached around 15%, calculated as D-allose as a percentage of reaction mixture after 2 hrs of reaction. The results of the bioconversion are depicted in FIG. 11.

Figure 8A:
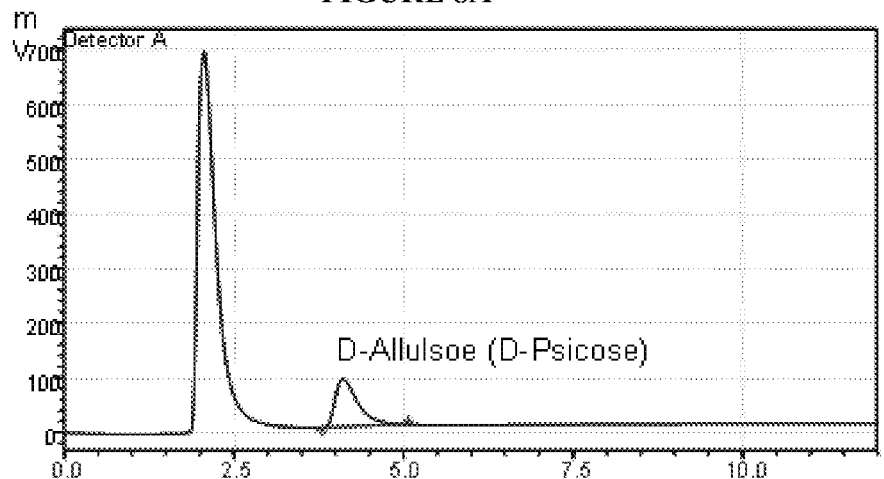
FIGS. 8A-8C illustrate HPLC analysis of D-allulose to D-allose conversion.
Figure 8B:
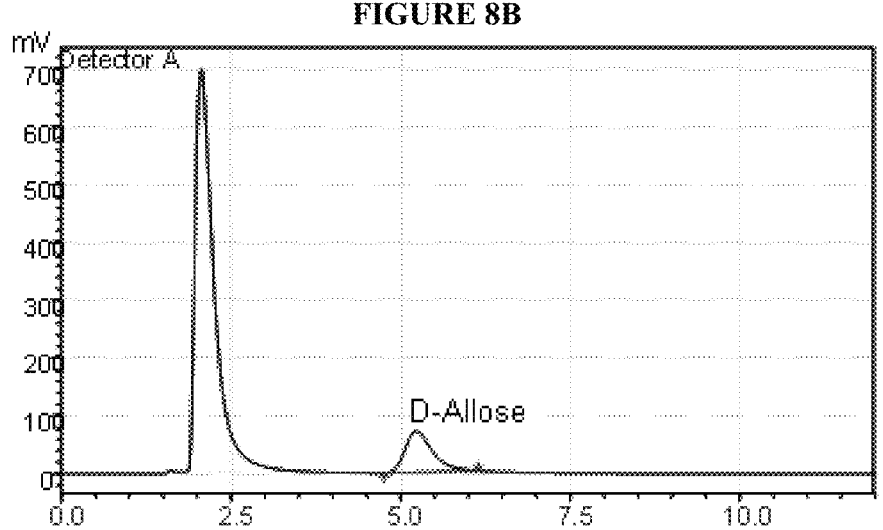
Figure 8C:
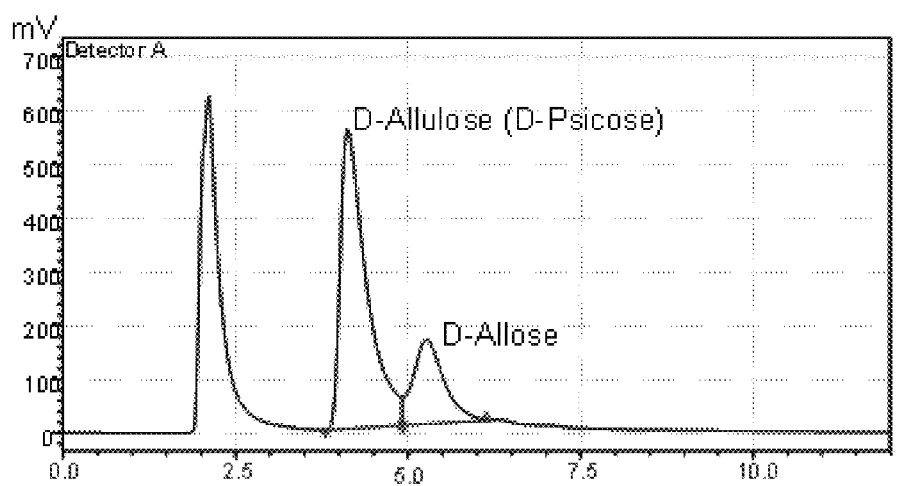

The reaction mixture was subjected to HPLC analysis to confirm the residual substrate and product formation. The product peak was confirmed with commercially available D-allulose (D-psicose) and D-allose (Sigma Aldrich) as substrate and product standards, respectively. The results of the studies are depicted in FIGS. 8A-8C. FIG. 8A depicts D-psicose standard chromatogram, FIG. 8B depicts D-allose standard chromatogram and FIG. 8C depicts D-psicose and D-allose bioconversion mixture chromatogram.

Example 11: Production of D-tagatose from D-galactose

The recombinant protein having isomerase activity prepared from *E. coli* was immobilized by using techniques known in the prior art or directly contacted with D-galactose solution for production of D-tagatose. The bioconversion conditions comprise maintaining the D-galactose substrate concentration between 20% and 95% (w/v) and 100 to 1000 units of the recombinant isomerase. For the present embodiment, the substrate was taken at a concentration of 100 g/L and 100 Units of immobilized enzyme was used. Bioconversion reaction was carried out in 20 mM Tris-HCl buffer containing 5 mM $MnCl_2$ at pH 8.0 at temperature between 60° C. The conversion of D-allulose to D-allose reached saturation at higher substrate concentration, preferably between 40% to 50% (w/v) at enzyme concentration between 400 to 600, preferably 500 units of enzyme with reaction time of about 6 h.

Figure 9:
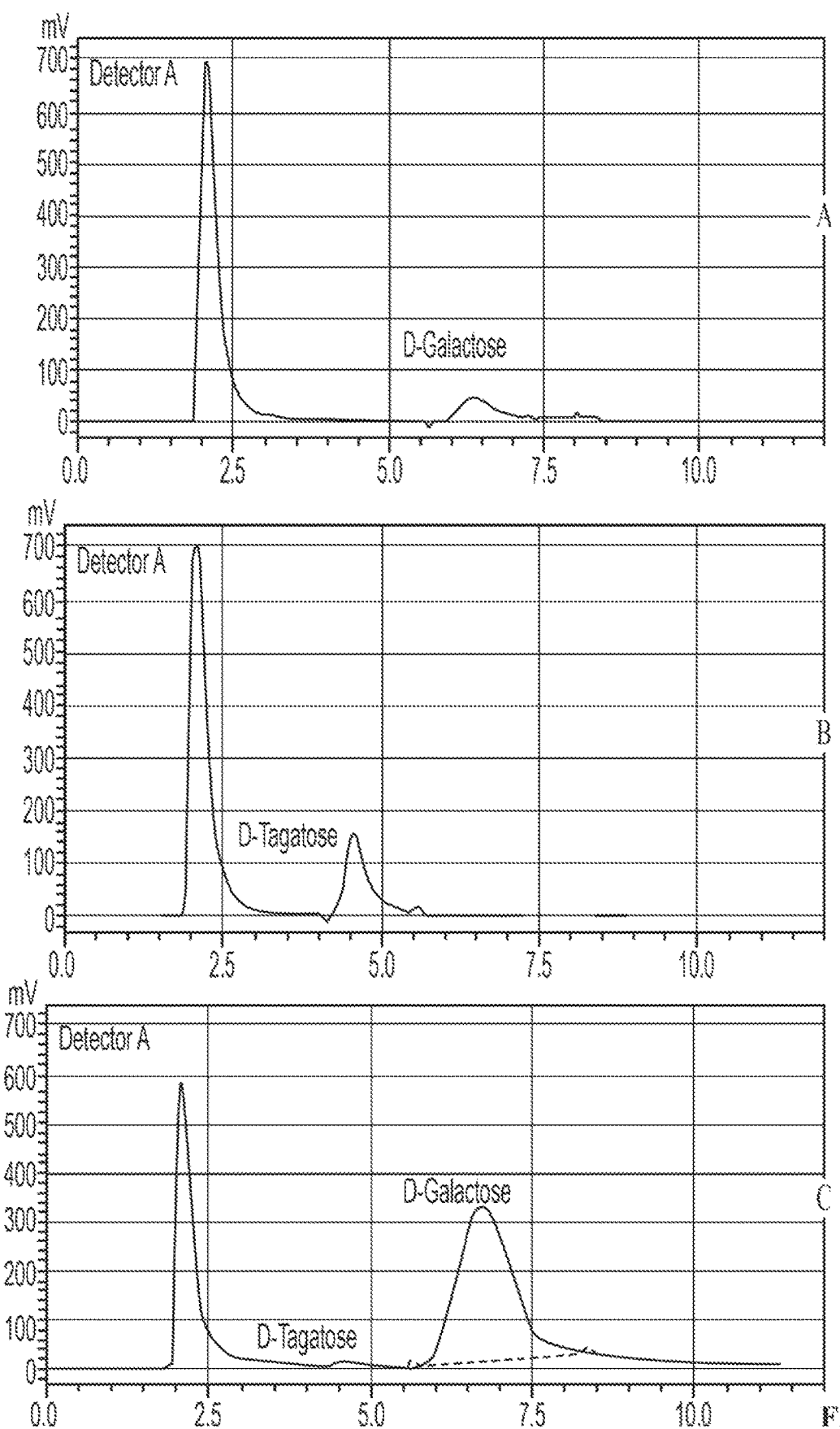
FIGS. 9A-9C illustrate HPLC analysis of D-galactose to D-tagatose conversion.

The reaction mixture was subjected to HPLC analysis to confirm the residual substrate and product formation. The product peak was confirmed with commercially available D-galactose and D-tagatose (Sigma Aldrich) as substrate and product standards, respectively. The results of the studies are depicted in FIGS. 9A-9C. FIG. 9A depicts D-galactose standard chromatogram, FIG. 9B depicts D-tagatose standard chromatogram and FIG. 9C depicts D-galactose and D-tagatose bioconversion mixture chromatogram.

The invention claimed is:

1. A modified nucleic acid comprising the nucleotide sequence of SEQ ID NO: 1, wherein the nucleic acid encodes a polypeptide having isomerase activity.

2. A vector comprising the nucleic acid as claimed in claim 1, wherein the modified nucleic acid is operably linked to a T7 promoter.

3. The vector as claimed in claim 2, wherein the vector is selected from a group comprising pET11 vector and pET23 vector.

4. The vector as claimed in claim 3, wherein the pET11 vector comprises the nucleotide sequence of SEQ ID NO: 3 and the pET23 vector comprises the nucleotide sequence of SEQ ID NO: 4.

5. A recombinant prokaryotic host cell comprising the vector as claimed in claim 2.

6. The recombinant host cell as claimed in claim 5, wherein the host cell is *Escherichia coli* JM 109.

7. A process for producing a recombinant host cell capable of expressing a polypeptide having isomerase activity, the said process comprising the steps of:
   a. constructing a recombinant vector harbouring the nucleic acid of SEQ ID NO: 1, wherein the nucleic acid is operably linked to a T7 promoter; and
   b. transforming a prokaryotic host cell with the recombinant vector to obtain a recombinant host cell.

8. The process as claimed in claim 7, wherein the vector is selected from a group comprising pET11 vector and pET23 vector.

9. The process as claimed in claim 8, wherein the pET11 vector comprises the nucleotide sequence of SEQ ID NO: 3 and the pET23 vector comprises the nucleotide sequence of SEQ ID NO: 4.

10. The process as claimed in claim 7, wherein the prokaryotic host cell is *Escherichia coli* JM 109.

11. A process for production of a protein having isomerase activity, said process comprising the steps of:
    a. culturing host cells transformed with a vector comprising the modified nucleic acid of SEQ ID NO: 1 in a suitable culture medium; and
    b. isolating and purifying a recombinant protein having isomerase activity expressed from the host cells.

12. A process for bioconversion of sugars into their respective isomers, said process comprising the steps of:
    a. culturing host cells as claimed in claim 5 in a suitable culture medium;
    b. isolating and purifying a recombinant protein having isomerase activity expressed from the host cells;
    c. contacting the recombinant protein with a suitable substrate in a bioreactor, wherein the reaction temperature is maintained between 50° C. to 80° C., the pH is maintained between 4 and 10 and the reaction time is in a range from 3 to 5 hrs;
    d. purifying the product from the reaction mixture.

13. The process as claimed in claim 12, wherein substrate is selected from a group comprising D-xylose, D-glucose, D-galactose, D-mannose, D-allulose, D-rhamnose and D-ribose.

14. The process as claimed in claim 12, wherein the bioreactor is selected from a group comprising packed bed reactor and enzyme membrane reactor.

15. The process as claimed in claim 12, wherein the recombinant protein having isomerase activity is immobilized on an immobilization matrix.

* * * * *